United States Patent
Schantz

(10) Patent No.: US 8,951,756 B2
(45) Date of Patent: Feb. 10, 2015

(54) ALKALINE FEED

(75) Inventor: Christian Schantz, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 209 days.

(21) Appl. No.: 13/217,540

(22) Filed: Aug. 25, 2011

(65) Prior Publication Data

US 2013/0323783 A1  Dec. 5, 2013

(30) Foreign Application Priority Data

Aug. 30, 2010  (EP) .................................... 10008997

(51) Int. Cl.
| | | |
|---|---|---|
| *C12P 21/06* | (2006.01) | |
| *C12P 21/04* | (2006.01) | |
| *C12N 1/20* | (2006.01) | |
| *C07H 21/04* | (2006.01) | |
| *C12P 21/00* | (2006.01) | |
| *C12P 21/02* | (2006.01) | |

(52) U.S. Cl.
CPC . *C12P 21/00* (2013.01); *C12N 1/20* (2013.01); *C12P 21/02* (2013.01)
USPC ... 435/69.1; 435/69.7; 435/252.8; 435/253.6; 536/23.4; 536/23.5; 530/350

(58) Field of Classification Search
CPC ............................... C12N 15/133; C12N 15/85
USPC ......... 435/69.1, 69.7, 252.8, 253.6; 536/23.4, 536/23.5; 530/350
See application file for complete search history.

(56) References Cited

U.S. PATENT DOCUMENTS

2002/0156007 A1* 10/2002 Graversen et al. .............. 514/12

FOREIGN PATENT DOCUMENTS

| WO | 97/21829 A1 | 6/1997 |
|---|---|---|
| WO | 02/38609 A2 | 5/2002 |
| WO | 03/483741 A1 | 6/2003 |

OTHER PUBLICATIONS (Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Karathanasis et al., Isoaltion and characterization of the human apolipoprotein A-I gene. PNAS. 80: pp. 6147-6151, 1983.*
Ryan et al., Optimized bacterial expression of human apolipoprotein A-I. Prot. Exp. and Purif. 27: 98-103, 2003.*
Whisstock et al., Prediction of protein function from protein sequence and structure. Quart. Rev. BioPhys. 36: 307-340, 2003.*
Sezonov et al., *Escherichia coli* Physiology in Luria-Bertani Broth. Jnl. of Bact. 189: 8746-8749, 2007.*
Sang Yup Lee. High cell-density culture of *Escherichia coli*. Trends in Biotechnology. 14(3), 98-105, 1996, in IDS, #6.*
(Choi et al., Production of recombinant proteins by high cell density culture of *Escherichia coli*. Chemical Engineering Science 61: 876-885. 2006.*
Horn et al., "High volumetric yields of funtional dimeric miniantibodies in *Escherichia coli*, using an optimized expression vector and high-cell-density fermentation under non-limited growth conditions" Appl Microbiol Biotechol. 46(5-6):524-32 (Dec. 1996).
Yee et al., "Defined media optimization for growth of recombinant *Escherichia coli* X90" Biotechnol Bioeng. 41(2):221-30 (Jan. 1993).
Sang, "High cell-density culture of *Escherichia coli*" Trends in Biotechnology 14(3):98-105 (Mar. 1996).

* cited by examiner

*Primary Examiner* — Ganapathirama Raghu
(74) *Attorney, Agent, or Firm* — Hoffman-La Roche Inc.

(57) ABSTRACT

A method for cultivating a bacterial cell comprising the addition of an amino acid in an alkaline solution used for pH regulation. Also an aspect is a method for producing a polypeptide comprising the steps of a) providing a bacterial cell comprising a nucleic acid encoding the polypeptide, b) cultivating the provided cell, c) adjusting the pH value during the cultivating with a basic solution comprising an amino acid, d) recovering the polypeptide from the cell or the cultivation medium and thereby producing the polypeptide.

11 Claims, 4 Drawing Sheets

SEQUENCE LISTING

```
<160> NUMBER OF SEQ ID NOS: 38

<210> SEQ ID NO 1
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (1)

<400> SEQUENCE: 1

Ala Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125
```

```
Ser Lys Asp Leu Glu Glu Val Lys Ala Lys Val Gln Pro Tyr Leu Asp
        130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285

<210> SEQ ID NO 2
<211> LENGTH: 283
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I (2)

<400> SEQUENCE: 2

Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val Asp Glu Pro Pro Gln Ser Pro Trp
        35                  40                  45

Asp Arg Val Lys Asp Leu Ala Thr Val Tyr Val Asp Val Leu Lys Asp
50                  55                  60

Ser Gly Arg Asp Tyr Val Ser Gln Phe Glu Gly Ser Ala Leu Gly Lys
65                  70                  75                  80

Gln Leu Asn Leu Lys Leu Leu Asp Asn Trp Asp Ser Val Thr Ser Thr
                85                  90                  95

Phe Ser Lys Leu Arg Glu Gln Leu Gly Pro Val Thr Gln Glu Phe Trp
            100                 105                 110

Asp Asn Leu Glu Lys Glu Thr Glu Gly Leu Arg Gln Glu Met Ser Lys
        115                 120                 125

Asp Leu Glu Glu Val Lys Ala Lys Val Gln Pro Tyr Leu Asp Asp Phe
130                 135                 140

Gln Lys Lys Trp Gln Glu Glu Met Glu Leu Tyr Arg Gln Lys Val Glu
145                 150                 155                 160

Pro Leu Arg Ala Glu Leu Gln Glu Gly Ala Arg Gln Lys Leu His Glu
                165                 170                 175

Leu Gln Glu Lys Leu Ser Pro Leu Gly Glu Glu Met Arg Asp Arg Ala
            180                 185                 190

Arg Ala His Val Asp Ala Leu Arg Thr His Leu Ala Pro Tyr Ser Asp
        195                 200                 205
```

```
Glu Leu Arg Gln Arg Leu Ala Ala Arg Leu Glu Ala Leu Lys Glu Asn
    210                 215                 220

Gly Gly Ala Arg Leu Ala Glu Tyr His Ala Lys Ala Thr Glu His Leu
225                 230                 235                 240

Ser Thr Leu Ser Glu Lys Ala Lys Pro Ala Leu Glu Asp Leu Arg Gln
                245                 250                 255

Gly Leu Leu Pro Val Leu Glu Ser Phe Lys Val Ser Phe Leu Ser Ala
            260                 265                 270

Leu Glu Glu Tyr Thr Lys Lys Leu Asn Thr Gln
        275                 280

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (1)

<400> SEQUENCE: 3

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      Apolipoprotein A-I mimetic (2)

<400> SEQUENCE: 4

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 5
<211> LENGTH: 267
<212> TYPE: PRT
<213> ORGANISM: Homo sapiens

<400> SEQUENCE: 5

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110
```

```
Asp Leu Glu Glu Val Lys Ala Lys Val Gln Pro Tyr Leu Asp Asp Phe
            115                 120                 125

Gln Lys Lys Trp Gln Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Met Arg Asp Arg Ala
            165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
            210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
            245                 250                 255

Leu Glu Glu Tyr Thr Lys Lys Leu Asn Thr Gln
            260                 265

<210> SEQ ID NO 6
<211> LENGTH: 100
<212> TYPE: PRT
<213> ORGANISM: Homo sapiens

<400> SEQUENCE: 6

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
            35                  40                  45

Met Glu Lys Val Lys Ser Pro Glu Leu Gln Ala Glu Ala Lys Ser Tyr
50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 7
<211> LENGTH: 396
<212> TYPE: PRT
<213> ORGANISM: Homo sapiens

<400> SEQUENCE: 7

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60
```

-continued

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 8
<211> LENGTH: 366
<212> TYPE: PRT
<213> ORGANISM: Homo sapiens

<400> SEQUENCE: 8

Met Ala Ser Met Ala Ala Val Leu Thr Trp Ala Leu Ala Leu Leu Ser
 1               5                  10                  15

Ala Phe Ser Ala Thr Gln Ala Arg Lys Gly Phe Trp Asp Tyr Phe Ser
                20                  25                  30

Gln Thr Ser Gly Asp Lys Gly Arg Val Glu Gln Ile His Gln Gln Lys
            35                  40                  45

```
Met Ala Arg Glu Pro Ala Thr Leu Lys Asp Ser Leu Glu Gln Asp Leu
 50                  55                  60

Asn Asn Met Asn Lys Phe Leu Glu Lys Leu Arg Pro Leu Ser Gly Ser
 65                  70                  75                  80

Glu Ala Pro Arg Leu Pro Gln Asp Pro Val Gly Met Arg Arg Gln Leu
                 85                  90                  95

Gln Glu Glu Leu Glu Glu Val Lys Ala Arg Leu Gln Pro Tyr Met Ala
            100                 105                 110

Glu Ala His Glu Leu Val Gly Trp Asn Leu Glu Gly Leu Arg Gln Gln
            115                 120                 125

Leu Lys Pro Tyr Thr Met Asp Leu Met Glu Gln Val Ala Leu Arg Val
130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
            195                 200                 205

Leu His Arg Ser Val Ala Pro His Ala Pro Ala Ser Pro Ala Arg Leu
210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ser Arg Ala Phe Ala Gly Thr Gly Thr Glu Glu Gly Ala Gly Pro
            260                 265                 270

Asp Pro Gln Met Leu Ser Glu Val Arg Gln Arg Leu Gln Ala Phe
            275                 280                 285

Arg Gln Asp Thr Tyr Leu Gln Ile Ala Ala Phe Thr Arg Ala Ile Asp
            290                 295                 300

Gln Glu Thr Glu Glu Val Gln Gln Gln Leu Ala Pro Pro Pro Pro Gly
305                 310                 315                 320

His Ser Ala Phe Ala Pro Glu Phe Gln Gln Thr Asp Ser Gly Lys Val
                325                 330                 335

Leu Ser Lys Leu Gln Ala Arg Leu Asp Asp Leu Trp Glu Asp Ile Thr
            340                 345                 350

His Ser Leu His Asp Gln Gly His Ser His Leu Gly Asp Pro
            355                 360                 365

<210> SEQ ID NO 9
<211> LENGTH: 267
<212> TYPE: PRT
<213> ORGANISM: Homo sapiens

<400> SEQUENCE: 9

Met Lys Ala Ala Val Leu Thr Leu Ala Val Leu Phe Leu Thr Gly Ser
 1                5                 10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
             35                 40                  45

Ser Gly Arg Asp Tyr Val Ser Gln Phe Glu Gly Ser Ala Leu Gly Lys
         50                  55                  60
```

```
Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 10
<211> LENGTH: 267
<212> TYPE: PRT
<213> ORGANISM: Homo sapiens

<400> SEQUENCE: 10

Met Lys Ala Ala Val Leu Thr Leu Ala Val Leu Phe Leu Thr Gly Ser
 1                5                  10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175
```

```
Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 11
<211> LENGTH: 267
<212> TYPE: PRT
<213> ORGANISM: Homo sapiens

<400> SEQUENCE: 11

```
Met Lys Ala Thr Val Leu Thr Leu Ala Val Leu Phe Leu Thr Gly Ser
1               5                   10                  15

Gln Ala Arg His Phe Trp Gln Gln Asp Glu Pro Pro Gln Thr Pro Trp
            20                  25                  30

Asp Arg Val Lys Asp Leu Val Thr Val Tyr Val Glu Ala Leu Lys Asp
        35                  40                  45

Ser Gly Lys Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Val Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu His Glu Gly Thr Arg Gln Lys Leu His Glu
145                 150                 155                 160

Leu His Glu Lys Leu Ser Pro Leu Gly Glu Glu Val Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Ser Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Ser Thr Gln
            260                 265
```

<210> SEQ ID NO 12
<211> LENGTH: 265
<212> TYPE: PRT
<213> ORGANISM: Homo sapiens

<400> SEQUENCE: 12

Met Lys Ala Val Val Leu Thr Leu Ala Val Leu Phe Leu Thr Gly Ser
1               5                   10                  15

Gln Ala Arg His Phe Trp Gln Gln Asp Asp Pro Gln Ser Ser Trp Asp
            20                  25                  30

Arg Val Lys Asp Phe Ala Thr Val Tyr Val Glu Ala Ile Lys Asp Ser
        35                  40                  45

Gly Arg Asp Tyr Val Ala Gln Phe Glu Ala Ser Ala Leu Gly Lys Gln
    50                  55                  60

Leu Asn Leu Lys Leu Leu Asp Asn Trp Asp Thr Leu Ala Ser Thr Leu
65                  70                  75                  80

Ser Lys Val Arg Glu Gln Leu Gly Pro Val Thr Gln Glu Phe Trp Asp
                85                  90                  95

Asn Leu Glu Lys Glu Thr Ala Ser Leu Arg Gln Glu Met His Lys Asp
            100                 105                 110

Leu Glu Glu Val Lys Gln Lys Val Gln Pro Tyr Leu Asp Glu Phe Gln
        115                 120                 125

Lys Lys Trp His Glu Glu Val Glu Ile Tyr Arg Gln Lys Val Ala Pro
    130                 135                 140

Leu Gly Glu Glu Phe Arg Glu Gly Ala Arg Gln Lys Val Gln Glu Leu
145                 150                 155                 160

Gln Asp Lys Leu Ser Pro Leu Ala Gln Glu Leu Arg Asp Arg Ala Arg
                165                 170                 175

Ala His Val Glu Thr Leu Arg Gln Gln Leu Ala Pro Tyr Ser Asp Asp
            180                 185                 190

Leu Arg Gln Arg Leu Thr Ala Arg Leu Glu Ala Leu Lys Glu Gly Gly
        195                 200                 205

Gly Ser Leu Ala Glu Tyr His Ala Lys Ala Ser Glu Gln Leu Lys Ala
    210                 215                 220

Leu Gly Glu Lys Ala Lys Pro Val Leu Glu Asp Leu Arg Gln Gly Leu
225                 230                 235                 240

Leu Pro Val Leu Glu Ser Leu Lys Val Ser Ile Leu Ala Ala Ile Asp
                245                 250                 255

Glu Ala Ser Lys Lys Leu Asn Ala Gln
            260                 265

<210> SEQ ID NO 13
<211> LENGTH: 264
<212> TYPE: PRT
<213> ORGANISM: Homo sapiens

<400> SEQUENCE: 13

Met Lys Ala Trp Leu Thr Leu Ala Val Leu Phe Leu Thr Gly Ser Gln
1               5                   10                  15

Ala Arg His Phe Trp Gln Gln Asp Asp Pro Gln Ser Pro Trp Asp Arg
            20                  25                  30

Val Lys Asp Phe Ala Thr Val Tyr Val Asp Ala Ile Lys Asp Ser Gly
        35                  40                  45

Arg Asp Tyr Val Ala Gln Phe Glu Ala Ser Ala Leu Gly Lys His Leu
    50                  55                  60

```
Asn Leu Lys Leu Leu Asp Asn Trp Asp Ser Leu Gly Ser Thr Phe Thr
 65                  70                  75                  80

Lys Val Arg Glu Gln Leu Gly Pro Val Thr Gln Glu Phe Trp Asp Asn
                 85                  90                  95

Leu Glu Lys Glu Thr Glu Ala Leu Arg Gln Glu Met Ser Lys Asp Leu
            100                 105                 110

Glu Glu Val Lys Lys Val Gln Pro Tyr Leu Asp Asp Phe Gln Asn
        115                 120                 125

Lys Trp Gln Glu Glu Met Glu Thr Tyr Arg Gln Lys Met Ala Pro Leu
    130                 135                 140

Gly Ala Glu Phe Arg Glu Gly Ala Arg Gln Lys Val Gln Glu Leu Gln
145                 150                 155                 160

Glu Lys Leu Ser Pro Leu Ala Glu Glu Leu Arg Asp Arg Leu Arg Ala
                165                 170                 175

His Val Glu Ala Leu Arg Gln His Val Ala Pro Tyr Ser Asp Asp Leu
            180                 185                 190

Arg Gln Arg Met Ala Ala Arg Phe Glu Ala Leu Lys Glu Gly Gly Gly
            195                 200                 205

Ser Leu Ala Glu Tyr Gln Ala Lys Ala Gln Glu Gln Leu Lys Ala Leu
    210                 215                 220

Gly Glu Lys Ala Lys Pro Ala Leu Glu Asp Leu Arg Gln Gly Leu Leu
225                 230                 235                 240

Pro Val Leu Glu Asn Leu Lys Val Ser Ile Leu Ala Ala Ile Asp Glu
                245                 250                 255

Ala Ser Lys Lys Leu Asn Ala Gln
            260

<210> SEQ ID NO 14
<211> LENGTH: 266
<212> TYPE: PRT
<213> ORGANISM: Homo sapiens

<400> SEQUENCE: 14

Met Lys Ala Ala Leu Leu Thr Leu Ala Val Leu Phe Leu Thr Gly Ser
  1               5                  10                  15

Gln Ala Arg His Phe Trp Gln Gln Asp Glu Pro Gln Ser Pro Trp Asp
                 20                  25                  30

Arg Val Lys Asp Leu Ala Thr Val Tyr Val Asp Ala Val Lys Asp Ser
             35                  40                  45

Gly Arg Asp Tyr Val Ala Gln Phe Glu Ala Ser Ala Leu Gly Lys Gln
     50                  55                  60

Leu Asn Leu Lys Leu Leu Asp Asn Trp Asp Ser Leu Ser Ser Thr Val
 65                  70                  75                  80

Thr Lys Leu Arg Glu Gln Ile Gly Pro Val Thr Gln Glu Phe Trp Asp
                 85                  90                  95

Asn Leu Glu Lys Glu Thr Glu Val Leu Arg Gln Glu Met Ser Lys Asp
            100                 105                 110

Leu Glu Glu Val Lys Gln Lys Val Gln Pro Tyr Leu Asp Asp Phe Gln
        115                 120                 125

Lys Lys Trp Gln Glu Glu Val Glu Leu Tyr Arg Gln Lys Val Ala Pro
    130                 135                 140

Leu Gly Ser Glu Leu Arg Glu Gly Ala Arg Gln Lys Leu Gln Glu Leu
145                 150                 155                 160

Gln Glu Lys Leu Ser Pro Leu Ala Glu Glu Leu Arg Asp Arg Ala Arg
                165                 170                 175
```

```
Thr His Val Asp Ala Leu Arg Ala Gln Leu Ala Pro Tyr Ser Asp Asp
            180                 185                 190

Leu Arg Glu Arg Leu Ala Ala Arg Leu Glu Ala Leu Lys Glu Gly Gly
        195                 200                 205

Gly Ala Ser Leu Ala Glu Tyr His Ala Arg Ala Ser Glu Gln Leu Ser
        210                 215                 220

Ala Leu Gly Glu Lys Ala Arg Pro Ala Leu Glu Asp Leu Arg Gln Gly
225                 230                 235                 240

Leu Leu Pro Val Leu Glu Ser Phe Lys Val Ser Leu Leu Ala Ala Ile
                245                 250                 255

Asp Glu Ala Thr Lys Lys Leu Asn Ala Gln
            260                 265

<210> SEQ ID NO 15
<211> LENGTH: 206
<212> TYPE: PRT
<213> ORGANISM: Homo sapiens

<400> SEQUENCE: 15

Met Lys Ala Val Val Leu Thr Leu Ala Val Leu Phe Leu Thr Gly Ser
1               5                   10                  15

Gln Ala Arg His Phe Trp Gln Arg Asp Glu Pro Arg Ser Ser Trp Asp
            20                  25                  30

Lys Ile Lys Asp Phe Ala Thr Val Tyr Val Asp Thr Val Lys Asp Ser
        35                  40                  45

Gly Arg Glu Tyr Val Ala Gln Phe Glu Ala Ser Ala Phe Gly Lys Gln
    50                  55                  60

Leu Asn Leu Lys Leu Leu Asp Asn Trp Asp Ser Leu Ser Ser Thr Val
65                  70                  75                  80

Ser Lys Leu Gln Glu Gln Leu Gly Pro Val Thr Gln Glu Phe Trp Asp
                85                  90                  95

Asn Leu Glu Lys Glu Thr Glu Gly Leu Arg Glu Glu Met Asn Lys Asp
            100                 105                 110

Leu Gln Glu Val Arg Gln Lys Val Gln Pro Tyr Leu Asp Glu Phe Gln
        115                 120                 125

Lys Lys Trp Gln Glu Glu Val Glu Arg Tyr Arg Gln Lys Val Glu Pro
    130                 135                 140

Leu Gly Ala Glu Leu Arg Glu Ser Ala Arg Gln Lys Leu Thr Glu Leu
145                 150                 155                 160

Gln Glu Lys Leu Ser Pro Leu Ala Glu Glu Leu Arg Asp Ser Ala Arg
                165                 170                 175

Thr His Val Gly Leu Leu Pro Val Leu Glu Ser Phe Lys Ala Ser Val
            180                 185                 190

Gln Asn Val Leu Asp Glu Ala Thr Lys Lys Leu Asn Thr Gln
        195                 200                 205

<210> SEQ ID NO 16
<211> LENGTH: 265
<212> TYPE: PRT
<213> ORGANISM: Homo sapiens

<400> SEQUENCE: 16

Met Lys Ala Val Val Leu Thr Leu Ala Val Leu Phe Leu Thr Gly Ser
1               5                   10                  15

Gln Ala Arg His Phe Trp Gln Gln Asp Glu Pro Gln Ser Ser Trp Asp
            20                  25                  30
```

```
Arg Val Arg Asp Leu Ala Asn Val Tyr Val Asp Ala Val Lys Glu Ser
        35                  40                  45

Gly Arg Glu Tyr Val Ser Gln Leu Glu Ala Ser Ala Leu Gly Lys Gln
 50                  55                  60

Leu Asn Leu Lys Leu Val Asp Asn Trp Asp Thr Leu Gly Ser Thr Phe
 65                  70                  75                  80

Gln Lys Val His Glu His Leu Gly Pro Val Ala Gln Glu Phe Trp Glu
                 85                  90                  95

Lys Leu Glu Lys Glu Thr Glu Glu Leu Arg Arg Glu Ile Asn Lys Asp
            100                 105                 110

Leu Glu Asp Val Arg Gln Lys Thr Gln Pro Phe Leu Asp Glu Ile Gln
        115                 120                 125

Lys Lys Trp Gln Glu Asp Leu Glu Arg Tyr Arg Gln Lys Val Glu Pro
 130                 135                 140

Leu Ser Ala Gln Leu Arg Glu Gly Ala Arg Gln Lys Leu Met Glu Leu
145                 150                 155                 160

Gln Glu Gln Val Thr Pro Leu Gly Glu Asp Leu Arg Asp Ser Val Arg
                165                 170                 175

Ala Tyr Ala Asp Thr Leu Arg Thr Gln Leu Ala Pro Tyr Ser Glu Gln
            180                 185                 190

Met Arg Lys Thr Leu Gly Ala Arg Leu Glu Ala Ile Lys Glu Gly Gly
        195                 200                 205

Ser Ala Ser Leu Ala Glu Tyr His Ala Lys Ala Ser Glu Gln Leu Ser
 210                 215                 220

Ala Leu Gly Glu Lys Ala Lys Pro Val Leu Glu Asp Ile His Gln Gly
225                 230                 235                 240

Leu Met Pro Met Trp Glu Ser Phe Lys Thr Gly Val Leu Asn Val Ile
                245                 250                 255

Asp Glu Ala Ala Lys Lys Leu Thr Ala
            260                 265

<210> SEQ ID NO 17
<211> LENGTH: 264
<212> TYPE: PRT
<213> ORGANISM: Homo sapiens

<400> SEQUENCE: 17

Met Lys Ala Val Val Leu Ala Val Ala Leu Val Phe Leu Thr Gly Ser
 1                   5                  10                  15

Gln Ala Trp His Val Trp Gln Gln Asp Glu Pro Gln Ser Gln Trp Asp
                 20                  25                  30

Lys Val Lys Asp Phe Ala Asn Val Tyr Val Asp Ala Val Lys Asp Ser
            35                  40                  45

Gly Arg Asp Tyr Val Ser Gln Phe Glu Ser Ser Ser Leu Gly Gln Gln
 50                  55                  60

Leu Asn Leu Asn Leu Leu Glu Asn Trp Asp Thr Leu Gly Ser Thr Val
 65                  70                  75                  80

Ser Gln Leu Gln Glu Arg Leu Gly Pro Leu Thr Arg Asp Phe Trp Asp
                 85                  90                  95

Asn Leu Glu Lys Glu Thr Asp Trp Val Arg Gln Glu Met Asn Lys Asp
            100                 105                 110

Leu Glu Glu Val Lys Gln Lys Val Gln Pro Tyr Leu Asp Glu Phe Gln
        115                 120                 125

Lys Lys Trp Lys Glu Asp Val Glu Leu Tyr Arg Gln Lys Val Ala Pro
 130                 135                 140
```

```
Leu Gly Ala Glu Leu Gln Glu Ser Ala Arg Gln Lys Leu Gln Glu Leu
145                 150                 155                 160

Gln Gly Arg Leu Ser Pro Val Ala Glu Glu Phe Arg Asp Arg Met Arg
                165                 170                 175

Thr His Val Asp Ser Leu Arg Thr Gln Leu Ala Pro His Ser Glu Gln
                180                 185                 190

Met Arg Glu Ser Leu Ala Gln Arg Leu Ala Glu Leu Lys Ser Asn Pro
                195                 200                 205

Thr Leu Asn Glu Tyr His Thr Arg Ala Lys Thr His Leu Lys Thr Leu
            210                 215                 220

Gly Glu Lys Ala Arg Pro Ala Leu Glu Asp Leu Arg His Ser Leu Met
225                 230                 235                 240

Pro Met Leu Glu Thr Leu Lys Thr Lys Ala Gln Ser Val Ile Asp Lys
                245                 250                 255

Ala Ser Glu Thr Leu Thr Ala Gln
                260
```

<210> SEQ ID NO 18
<211> LENGTH: 259
<212> TYPE: PRT
<213> ORGANISM: Homo sapiens

<400> SEQUENCE: 18

```
Met Lys Ala Ala Val Leu Ala Val Ala Leu Val Phe Leu Thr Gly Cys
1               5                   10                  15

Gln Ala Trp Glu Phe Trp Gln Gln Asp Glu Pro Gln Ser Gln Trp Asp
            20                  25                  30

Arg Val Lys Asp Phe Ala Thr Val Tyr Val Asp Ala Val Lys Asp Ser
        35                  40                  45

Gly Arg Asp Tyr Val Ser Gln Phe Glu Ser Ser Thr Leu Gly Lys Gln
    50                  55                  60

Leu Asn Leu Asn Leu Leu Asp Asn Trp Asp Thr Leu Gly Ser Thr Val
65                  70                  75                  80

Gly Arg Leu Gln Glu Gln Leu Gly Pro Val Thr Gln Glu Phe Trp Ala
                85                  90                  95

Asn Leu Glu Lys Glu Thr Asp Trp Leu Arg Asn Glu Met Asn Lys Asp
            100                 105                 110

Leu Glu Asn Val Lys Gln Lys Met Gln Pro His Leu Asp Glu Phe Gln
        115                 120                 125

Glu Lys Trp Asn Glu Glu Val Glu Ala Tyr Arg Gln Lys Leu Glu Pro
    130                 135                 140

Leu Gly Thr Glu Leu His Lys Asn Ala Lys Glu Met Gln Arg His Leu
145                 150                 155                 160

Lys Val Val Ala Glu Glu Phe Arg Asp Arg Met Arg Val Asn Ala Asp
                165                 170                 175

Ala Leu Arg Ala Lys Phe Gly Leu Tyr Ser Asp Gln Met Arg Glu Asn
            180                 185                 190

Leu Ala Gln Arg Leu Thr Glu Ile Arg Asn His Pro Thr Leu Ile Glu
        195                 200                 205

Tyr His Thr Lys Ala Gly Asp His Leu Arg Thr Leu Gly Glu Lys Ala
    210                 215                 220

Lys Pro Ala Leu Asp Asp Leu Gly Gln Gly Leu Met Pro Val Leu Glu
225                 230                 235                 240
```

```
Ala Trp Lys Ala Lys Ile Met Ser Met Ile Asp Glu Ala Lys Lys Lys
                245                 250                 255

Leu Asn Ala
```

<210> SEQ ID NO 19
<211> LENGTH: 241
<212> TYPE: PRT
<213> ORGANISM: Homo sapiens

<400> SEQUENCE: 19

```
Asp Glu Ala Lys Ser Tyr Trp Asp Gln Ile Lys Asp Met Leu Thr Val
1               5                   10                  15

Tyr Val Asp Thr Ala Lys Asp Ser Gly Lys Asp Tyr Leu Thr Ser Leu
                20                  25                  30

Asp Thr Ser Ala Leu Gly Gln Gln Leu Asn Lys Lys Leu Ala Asp Asn
            35                  40                  45

Trp Asp Thr Val Ser Ser Ala Leu Leu Lys Ala Arg Glu Gln Met Lys
50                  55                  60

Pro Ile Ala Met Glu Phe Trp Gly Asn Leu Glu Lys Asp Thr Glu Gly
65                  70                  75                  80

Leu Arg Gln Thr Val Ser Lys Asp Leu Glu Leu Val Lys Glu Lys Val
                85                  90                  95

Gln Pro Tyr Leu Asp Ser Phe Gln Lys Lys Val Glu Glu Leu Glu
                100                 105                 110

Leu Tyr Arg Gln Lys Val Ala Pro Leu Ser Ala Glu Trp Arg Glu Gln
            115                 120                 125

Ala Arg Gln Lys Ala Gln Glu Leu Gln Gln Lys Ala Gly Glu Leu Gly
            130                 135                 140

Gln Gln His Arg Asp Arg Val Arg Thr His Val Asp Ala Leu Arg Thr
145                 150                 155                 160

Asp Leu Ala Pro Tyr Gly Glu Glu Ala Arg Lys Leu Leu Gln Arg
                165                 170                 175

Leu Gln Asp Ile Lys Ala Lys Ser Gly Asp Leu Ala Glu Tyr Gln Thr
                180                 185                 190

Lys Leu Ser Glu His Leu Lys Ser Phe Gly Lys Ala Gln Pro Thr
            195                 200                 205

Leu Gln Asp Leu Arg His Gly Leu Glu Pro Leu Trp Glu Gly Ile Lys
210                 215                 220

Ala Gly Ala Met Ser Met Leu Glu Gly Leu Lys Lys Leu Asn Ser
225                 230                 235                 240

Gln
```

<210> SEQ ID NO 20
<211> LENGTH: 264
<212> TYPE: PRT
<213> ORGANISM: Homo sapiens

<400> SEQUENCE: 20

```
Met Arg Gly Val Leu Val Thr Leu Ala Val Leu Phe Leu Thr Gly Thr
1               5                   10                  15

Gln Ala Arg Ser Phe Trp Gln His Asp Glu Pro Gln Thr Pro Leu Asp
                20                  25                  30

Arg Ile Arg Asp Met Val Asp Val Tyr Leu Glu Thr Val Lys Ala Ser
            35                  40                  45

Gly Lys Asp Ala Ile Ala Gln Phe Glu Ser Ser Ala Val Gly Lys Gln
50                  55                  60
```

```
Leu Asp Leu Lys Leu Ala Asp Asn Leu Asp Thr Leu Ser Ala Ala Ala
 65                  70                  75                  80

Ala Lys Leu Arg Glu Asp Met Ala Pro Tyr Tyr Lys Glu Val Arg Glu
                 85                  90                  95

Met Trp Leu Lys Asp Thr Glu Ala Leu Arg Ala Glu Leu Thr Lys Asp
            100                 105                 110

Leu Glu Glu Val Lys Glu Lys Ile Arg Pro Phe Leu Asp Gln Phe Ser
        115                 120                 125

Ala Lys Trp Thr Glu Glu Leu Glu Gln Tyr Arg Gln Arg Leu Thr Pro
    130                 135                 140

Val Ala Gln Glu Leu Lys Glu Leu Thr Lys Gln Lys Val Glu Leu Met
145                 150                 155                 160

Gln Ala Lys Leu Thr Pro Val Ala Glu Ala Arg Asp Arg Leu Arg
                165                 170                 175

Gly His Val Glu Glu Leu Arg Lys Asn Leu Ala Pro Tyr Ser Asp Glu
            180                 185                 190

Leu Arg Gln Lys Leu Ser Gln Lys Leu Glu Glu Ile Arg Glu Lys Gly
        195                 200                 205

Ile Pro Gln Ala Ser Glu Tyr Gln Ala Lys Val Met Glu Gln Leu Ser
    210                 215                 220

Asn Leu Arg Glu Lys Met Thr Pro Leu Val Gln Glu Phe Arg Glu Arg
225                 230                 235                 240

Leu Thr Pro Tyr Ala Glu Asn Leu Lys Asn Arg Leu Ile Ser Phe Leu
                245                 250                 255

Asp Glu Leu Gln Lys Ser Val Ala
            260

<210> SEQ ID NO 21
<211> LENGTH: 264
<212> TYPE: PRT
<213> ORGANISM: Homo sapiens

<400> SEQUENCE: 21

Met Arg Gly Val Leu Val Thr Leu Ala Val Leu Phe Leu Thr Gly Thr
 1               5                  10                  15

Gln Ala Arg Ser Phe Trp Gln His Asp Asp Pro Gln Thr Pro Leu Asp
                 20                  25                  30

Arg Ile Arg Asp Met Leu Asp Val Tyr Leu Glu Thr Val Lys Ala Ser
             35                  40                  45

Gly Lys Asp Ala Ile Ser Gln Phe Glu Ser Ser Ala Val Gly Lys Gln
         50                  55                  60

Leu Asp Leu Lys Leu Ala Asp Asn Leu Asp Thr Leu Ser Ala Ala Ala
 65                  70                  75                  80

Ala Lys Leu Arg Glu Asp Met Thr Pro Tyr Tyr Arg Glu Val Arg Glu
                 85                  90                  95

Met Trp Leu Lys Asp Thr Glu Ala Leu Arg Ala Glu Leu Thr Lys Asp
            100                 105                 110

Leu Glu Glu Val Lys Glu Lys Ile Arg Pro Phe Leu Asp Gln Phe Ser
        115                 120                 125

Ala Lys Trp Thr Glu Glu Val Glu Gln Tyr Arg Gln Arg Leu Ala Pro
    130                 135                 140

Val Ala Gln Glu Leu Lys Asp Leu Thr Lys Gln Lys Val Glu Leu Met
145                 150                 155                 160

Gln Ala Lys Leu Thr Pro Val Ala Glu Glu Val Arg Asp Arg Leu Arg
                165                 170                 175
```

```
Glu Gln Val Glu Glu Leu Arg Lys Asn Leu Ala Pro Tyr Ser Ser Glu
            180                 185                 190

Leu Arg Gln Lys Leu Ser Gln Lys Leu Glu Glu Ile Arg Glu Arg Gly
        195                 200                 205

Ile Pro Gln Ala Ser Glu Tyr Gln Ala Lys Val Val Glu Gln Leu Ser
    210                 215                 220

Asn Leu Arg Glu Lys Met Thr Pro Leu Val Gln Glu Phe Lys Glu Arg
225                 230                 235                 240

Leu Thr Pro Tyr Ala Glu Asn Leu Lys Asn Arg Leu Ile Asp Leu Leu
            245                 250                 255

Asp Glu Val Gln Lys Thr Met Ala
            260

<210> SEQ ID NO 22
<211> LENGTH: 264
<212> TYPE: PRT
<213> ORGANISM: Homo sapiens

<400> SEQUENCE: 22

Met Arg Val Val Val Thr Leu Ala Leu Leu Phe Leu Thr Gly Thr
1               5                   10                  15

Gln Ala Arg Tyr Phe Trp Gln His Asp Glu Pro Gln Ala Pro Leu Asp
            20                  25                  30

Arg Leu Arg Asp Leu Val Asp Val Tyr Leu Glu Thr Val Lys Ala Ser
        35                  40                  45

Gly Lys Asp Ala Ile Ala Gln Phe Glu Ala Ser Ala Val Gly Lys Gln
    50                  55                  60

Leu Asp Leu Lys Leu Ala Asp Asn Leu Asp Thr Leu Gly Ala Ala Ala
65                  70                  75                  80

Ala Lys Leu Arg Glu Asp Met Ala Pro Tyr Tyr Lys Glu Val Arg Glu
            85                  90                  95

Met Trp Leu Lys Asp Thr Glu Ser Leu Arg Ala Glu Leu Thr Lys Asp
            100                 105                 110

Leu Glu Glu Val Lys Glu Lys Ile Arg Pro Phe Leu Asp Gln Phe Ser
            115                 120                 125

Ala Lys Trp Thr Glu Glu Leu Glu Gln Tyr Arg Gln Arg Leu Ala Pro
130                 135                 140

Val Ala Glu Glu Leu Lys Glu Leu Thr Lys Gln Lys Val Glu Leu Met
145                 150                 155                 160

Gln Gln Lys Leu Thr Pro Val Ala Glu Glu Ala Arg Asp Arg Leu Arg
            165                 170                 175

Gly His Val Glu Glu Leu Arg Lys Asn Leu Ala Pro Tyr Ser Asp Glu
            180                 185                 190

Leu Arg Gln Lys Leu Ser Gln Lys Leu Glu Glu Ile Arg Glu Lys Gly
        195                 200                 205

Ile Pro Gln Ala Ala Glu Tyr Gln Ala Lys Val Val Glu Gln Leu Ser
    210                 215                 220

Asn Leu Arg Glu Lys Met Thr Pro Leu Val Gln Asp Phe Lys Glu Arg
225                 230                 235                 240

Leu Thr Pro Tyr Ala Glu Asn Leu Lys Thr Arg Phe Ile Ser Leu Leu
            245                 250                 255

Asp Glu Leu Gln Lys Thr Val Ala
            260
```

<210> SEQ ID NO 23
<211> LENGTH: 262
<212> TYPE: PRT
<213> ORGANISM: Homo sapiens

<400> SEQUENCE: 23

```
Met Lys Phe Leu Ala Leu Ala Leu Thr Ile Leu Leu Ala Ala Gly Thr
1               5                   10                  15

Gln Ala Phe Pro Met Gln Ala Asp Ala Pro Ser Gln Leu Glu His Val
            20                  25                  30

Lys Ala Ala Leu Ser Met Tyr Ile Ala Gln Val Lys Leu Thr Ala Gln
        35                  40                  45

Arg Ser Ile Asp Leu Leu Asp Asp Thr Glu Tyr Lys Glu Tyr Lys Met
50                  55                  60

Gln Leu Thr Gln Ser Leu Asp Asn Leu Gln Gln Tyr Ala Asp Ala Thr
65                  70                  75                  80

Ser Gln Ser Leu Ala Pro Tyr Ser Glu Ala Phe Gly Thr Gln Leu Thr
                85                  90                  95

Asp Ala Thr Ala Ala Val Arg Ala Glu Val Met Lys Asp Val Glu Glu
            100                 105                 110

Leu Arg Ser Gln Leu Glu Pro Lys Arg Ala Glu Leu Lys Glu Val Leu
        115                 120                 125

Asp Lys His Ile Asp Glu Tyr Arg Lys Lys Leu Glu Pro Leu Ile Lys
130                 135                 140

Glu His Ile Glu Leu Arg Arg Thr Glu Met Glu Ala Phe Arg Ala Lys
145                 150                 155                 160

Met Glu Pro Ile Val Glu Glu Leu Arg Ala Lys Val Ala Ile Asn Val
                165                 170                 175

Glu Glu Thr Lys Thr Lys Leu Met Pro Ile Val Glu Ile Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Glu Gln Met Ile Lys Ala Val Gly Glu Val Arg
210                 215                 220

Glu Lys Val Ser Pro Leu Ser Glu Asp Phe Lys Gly Asn Val Gly Pro
225                 230                 235                 240

Ala Ala Glu Gln Ala Lys Gln Lys Leu Leu Ala Phe Tyr Glu Thr Ile
                245                 250                 255

Ser Gln Ala Met Lys Ala
            260
```

<210> SEQ ID NO 24
<211> LENGTH: 262
<212> TYPE: PRT
<213> ORGANISM: Homo sapiens

<400> SEQUENCE: 24

```
Met Lys Phe Leu Ala Leu Ala Leu Thr Ile Leu Leu Ala Ala Ala Thr
1               5                   10                  15

Gln Ala Val Pro Met Gln Ala Asp Ala Pro Ser Gln Leu Glu His Val
            20                  25                  30

Lys Val Ala Met Met Glu Tyr Met Ala Gln Val Lys Glu Thr Gly Gln
        35                  40                  45

Arg Ser Ile Asp Leu Leu Asp Asp Thr Glu Phe Lys Glu Tyr Lys Val
50                  55                  60
```

```
Gln Leu Ser Gln Ser Leu Asp Asn Leu Gln Gln Tyr Ala Gln Thr Thr
 65                  70                  75                  80

Ser Gln Ser Leu Ala Pro Tyr Ser Glu Ala Phe Gly Ala Gln Leu Thr
                 85                  90                  95

Asp Ala Ala Ala Val Arg Ala Glu Val Met Lys Asp Val Glu Asp
            100                 105                 110

Val Arg Thr Gln Leu Glu Pro Lys Arg Ala Glu Leu Lys Glu Val Leu
            115                 120                 125

Asp Lys His Ile Asp Glu Tyr Arg Lys Lys Leu Glu Pro Leu Ile Lys
        130                 135                 140

Glu Ile Val Glu Gln Arg Arg Thr Glu Leu Ala Phe Arg Val Lys
145                 150                 155                 160

Met Glu Pro Val Val Glu Glu Met Arg Ala Lys Val Ser Thr Asn Val
                165                 170                 175

Glu Glu Thr Lys Ala Lys Leu Met Pro Ile Val Glu Thr Val Arg Ala
            180                 185                 190

Lys Leu Thr Glu Arg Leu Glu Glu Leu Arg Thr Leu Ala Ala Pro Tyr
        195                 200                 205

Ala Glu Glu Tyr Lys Glu Gln Met Phe Lys Ala Val Gly Glu Val Arg
    210                 215                 220

Glu Lys Val Gly Pro Leu Thr Asn Asp Phe Lys Gly Gln Val Gly Pro
225                 230                 235                 240

Ala Ala Glu Gln Ala Lys Glu Lys Leu Met Asp Phe Tyr Glu Thr Ile
                245                 250                 255

Ser Gln Ala Met Lys Ala
            260

<210> SEQ ID NO 25
<211> LENGTH: 258
<212> TYPE: PRT
<213> ORGANISM: Homo sapiens

<400> SEQUENCE: 25

Met Lys Phe Leu Val Leu Ala Leu Thr Ile Leu Leu Ala Ala Gly Thr
1               5                   10                  15

Gln Ala Phe Pro Met Gln Ala Asp Ala Pro Ser Gln Leu Glu His Val
                20                  25                  30

Lys Ala Ala Leu Asn Met Tyr Ile Ala Gln Val Lys Leu Thr Ala Gln
            35                  40                  45

Arg Ser Ile Asp Leu Leu Asp Asp Thr Glu Tyr Lys Glu Tyr Lys Met
    50                  55                  60

Gln Leu Ser Gln Ser Leu Asp Asn Leu Gln Gln Phe Ala Asp Ser Thr
 65                 70                  75                  80

Ser Lys Ser Trp Pro Pro Thr Pro Arg Ser Ser Ala Pro Ser Cys Asp
                85                  90                  95

Ala Thr Ala Thr Val Arg Ala Glu Val Met Lys Asp Val Glu Asp Val
            100                 105                 110

Arg Thr Gln Leu Glu Pro Lys Arg Ala Glu Leu Thr Glu Val Leu Asn
        115                 120                 125

Lys His Ile Asp Glu Tyr Arg Lys Lys Leu Glu Pro Leu Ile Lys Gln
    130                 135                 140

His Ile Glu Leu Arg Arg Thr Glu Met Asp Ala Phe Arg Ala Lys Ile
145                 150                 155                 160

Asp Pro Val Val Glu Glu Met Arg Ala Lys Val Ala Val Asn Val Glu
                165                 170                 175
```

Glu Thr Lys Thr Lys Leu Met Pro Ile Val Glu Ile Val Arg Ala Lys
            180                 185                 190

Leu Thr Glu Arg Leu Glu Glu Leu Arg Thr Leu Ala Ala Pro Tyr Ala
            195                 200                 205

Glu Glu Tyr Lys Glu Gln Met Phe Lys Ala Val Gly Glu Val Arg Glu
            210                 215                 220

Lys Val Ala Pro Leu Ser Glu Asp Phe Lys Ala Arg Trp Ala Pro Pro
225                 230                 235                 240

Pro Arg Arg Pro Ser Lys Ser Ser Trp Leu Ser Thr Arg Pro Ser Ala
            245                 250                 255

Arg Pro

<210> SEQ ID NO 26
<211> LENGTH: 262
<212> TYPE: PRT
<213> ORGANISM: Homo sapiens

<400> SEQUENCE: 26

Met Lys Phe Val Ala Leu Ala Leu Thr Leu Leu Ala Leu Gly Ser
1               5                   10                  15

Gln Ala Asn Leu Phe Gln Ala Asp Ala Pro Thr Gln Leu Glu His Tyr
            20                  25                  30

Lys Ala Ala Leu Val Tyr Leu Asn Gln Val Lys Asp Gln Ala Glu
            35                  40                  45

Lys Ala Leu Asp Asn Leu Asp Gly Thr Asp Tyr Glu Gln Tyr Lys Leu
50                  55                  60

Gln Leu Ser Glu Ser Leu Thr Lys Leu Gln Glu Tyr Ala Gln Thr Thr
65                  70                  75                  80

Ser Gln Ala Leu Thr Pro Tyr Ala Glu Thr Ile Ser Thr Gln Leu Met
            85                  90                  95

Glu Asn Thr Lys Gln Leu Arg Glu Arg Val Met Thr Asp Val Glu Asp
            100                 105                 110

Leu Arg Ser Lys Leu Glu Pro His Arg Ala Glu Leu Tyr Thr Ala Leu
            115                 120                 125

Gln Lys His Ile Asp Glu Tyr Arg Glu Lys Leu Glu Pro Val Phe Gln
130                 135                 140

Glu Tyr Ser Ala Leu Asn Arg Gln Asn Ala Glu Gln Leu Arg Ala Lys
145                 150                 155                 160

Leu Glu Pro Leu Met Asp Asp Ile Arg Lys Ala Phe Glu Ser Asn Ile
            165                 170                 175

Glu Glu Thr Lys Ser Lys Val Val Pro Met Val Glu Ala Val Arg Thr
            180                 185                 190

Lys Leu Thr Glu Arg Leu Glu Asp Leu Arg Thr Met Ala Ala Pro Tyr
            195                 200                 205

Ala Glu Glu Tyr Lys Glu Gln Leu Val Lys Ala Val Glu Glu Ala Arg
210                 215                 220

Glu Lys Ile Ala Pro His Thr Gln Asp Leu Gln Thr Arg Met Glu Pro
225                 230                 235                 240

Tyr Met Glu Asn Val Arg Thr Thr Phe Ala Gln Met Tyr Glu Thr Ile
            245                 250                 255

Ala Lys Ala Ile Gln Ala
            260

```
<210> SEQ ID NO 27
<211> LENGTH: 260
<212> TYPE: PRT
<213> ORGANISM: Homo sapiens

<400> SEQUENCE: 27

Met Lys Phe Ala Ala Leu Ala Leu Ala Leu Leu Ala Val Gly Ser
1               5                   10                  15

His Ala Ala Ser Met Gln Ala Asp Ala Pro Ser Gln Leu Asp His Ala
            20                  25                  30

Arg Ala Val Leu Asp Val Tyr Leu Thr Gln Val Lys Asp Met Ser Leu
        35                  40                  45

Arg Ala Val Asn Gln Leu Asp Asp Pro Gln Tyr Ala Glu Phe Lys Thr
    50                  55                  60

Asn Leu Ala Gln Arg Ile Glu Glu Met Tyr Thr Gln Ile Lys Thr Leu
65                  70                  75                  80

Gln Gly Ser Val Ser Pro Met Thr Asp Ser Phe Tyr Asn Thr Val Met
                85                  90                  95

Glu Val Thr Lys Asp Thr Arg Glu Ser Leu Asn Val Asp Leu Glu Ala
            100                 105                 110

Leu Lys Ser Ser Leu Ala Pro Gln Asn Glu Gln Leu Lys Gln Val Ile
        115                 120                 125

Glu Lys His Leu Asn Asp Tyr Arg Thr Leu Leu Thr Pro Ile Tyr Asn
    130                 135                 140

Asp Tyr Lys Thr Lys His Asp Glu Glu Met Ala Ala Leu Lys Thr Arg
145                 150                 155                 160

Leu Glu Pro Val Met Glu Glu Leu Arg Thr Lys Ile Gln Ala Asn Val
                165                 170                 175

Glu Glu Thr Lys Ala Val Leu Met Pro Met Val Glu Thr Val Arg Thr
            180                 185                 190

Lys Val Thr Glu Arg Leu Glu Ser Leu Arg Glu Val Val Gln Pro Tyr
        195                 200                 205

Val Gln Glu Tyr Lys Glu Gln Met Lys Gln Met Tyr Asp Gln Ala Gln
    210                 215                 220

Thr Val Asp Thr Asp Ala Leu Arg Thr Lys Ile Thr Pro Leu Val Glu
225                 230                 235                 240

Glu Ile Lys Val Lys Met Asn Ala Ile Phe Glu Ile Ile Ala Ala Ser
                245                 250                 255

Val Thr Lys Ser
        260

<210> SEQ ID NO 28
<211> LENGTH: 396
<212> TYPE: PRT
<213> ORGANISM: Homo sapiens

<400> SEQUENCE: 28

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60
```

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
        100                 105                 110

Leu Leu Pro His Ala Asn Glu Val Ser Gln Lys Ile Gly Asp Asn Leu
    115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 29
<211> LENGTH: 429
<212> TYPE: PRT
<213> ORGANISM: Homo sapiens

<400> SEQUENCE: 29

Met Phe Leu Lys Ala Val Val Leu Thr Leu Ala Leu Val Ala Val Thr
1               5                   10                  15

Gly Ala Arg Ala Glu Val Ser Ala Asp Gln Val Ala Thr Val Met Trp
            20                  25                  30

Asp Tyr Phe Ser Gln Leu Ser Ser Asn Ala Lys Glu Ala Val Glu His
        35                  40                  45

```
Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Arg Lys Glu Leu Glu Glu Val Arg Ala Arg
            100                 105                 110

Leu Leu Pro His Ala Asn Glu Val Ser Gln Lys Ile Gly Glu Asn Val
            115                 120                 125

Arg Glu Leu Gln Gln Arg Leu Glu Pro Tyr Thr Asp Gln Leu Arg Thr
130                 135                 140

Gln Val Asn Thr Gln Thr Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Thr Ser Leu Arg Pro His Ala Asp Gln Leu Lys Ala Lys Ile Asp Gln
            180                 185                 190

Asn Val Glu Glu Leu Lys Glu Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Ala Gln Glu Lys Leu Asn His Gln Leu Glu Gly
225                 230                 235                 240

Leu Ala Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Met Arg Gly Asn Leu Arg Gly Asn Thr Glu Gly Leu Gln Lys Ser
            275                 280                 285

Leu Ala Glu Leu Gly Gly His Leu Asp Arg His Val Glu Glu Phe Arg
290                 295                 300

Leu Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Asn Thr Leu
            355                 360                 365

Ser Leu Pro Glu Pro Glu Gln Gln Arg Glu Gln Gln Gln Glu Gln Gln
370                 375                 380

Gln Glu Gln Gln Gln Gln Gln Gln Gln Gln Glu Gln Gln Gln Gln Gln
385                 390                 395                 400

Gln Gln Gln Gln Arg Glu Gln Gln Gln Glu Gln Gln Gln Gln Glu Gln
                405                 410                 415

Gln Gln Glu Gln Val Gln Met Leu Ala Pro Leu Glu Ser
            420                 425

<210> SEQ ID NO 30
<211> LENGTH: 395
<212> TYPE: PRT
<213> ORGANISM: Homo sapiens
```

```
<400> SEQUENCE: 30

Met Phe Leu Lys Ala Ala Val Leu Thr Leu Ala Leu Val Ala Ile Thr
1               5                   10                  15

Gly Thr Arg Ala Glu Val Thr Ser Asp Gln Val Ala Asn Val Val Trp
            20                  25                  30

Asp Tyr Phe Thr Gln Leu Ser Asn Asn Ala Lys Glu Ala Val Glu Gln
        35                  40                  45

Phe Gln Lys Thr Asp Val Thr Gln Gln Leu Ser Thr Leu Phe Gln Asp
    50                  55                  60

Lys Leu Gly Asp Ala Ser Thr Tyr Ala Asp Gly Val His Asn Lys Leu
65                  70                  75                  80

Val Pro Phe Val Val Gln Leu Ser Gly His Leu Ala Lys Glu Thr Glu
                85                  90                  95

Arg Val Lys Glu Glu Ile Lys Lys Glu Leu Glu Asp Leu Arg Asp Arg
            100                 105                 110

Met Met Pro His Ala Asn Lys Val Thr Gln Thr Phe Gly Glu Asn Met
        115                 120                 125

Gln Lys Leu Gln Glu His Leu Lys Pro Tyr Ala Val Asp Leu Gln Asp
    130                 135                 140

Gln Ile Asn Thr Gln Thr Gln Glu Met Lys Leu Gln Leu Thr Pro Tyr
145                 150                 155                 160

Ile Gln Arg Met Gln Thr Thr Ile Lys Glu Asn Val Asp Asn Leu His
                165                 170                 175

Thr Ser Met Met Pro Leu Ala Thr Asn Leu Lys Asp Lys Phe Asn Arg
            180                 185                 190

Asn Met Glu Glu Leu Lys Gly His Leu Thr Pro Arg Ala Asn Glu Leu
        195                 200                 205

Lys Ala Thr Ile Asp Gln Asn Leu Glu Asp Leu Arg Arg Ser Leu Ala
    210                 215                 220

Pro Leu Thr Val Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Ala Lys Ile Asp Gln Leu Gln Lys Asn Leu Ala Pro Leu Val Glu
            260                 265                 270

Asp Val Gln Ser Lys Val Lys Gly Asn Thr Glu Gly Leu Gln Lys Ser
        275                 280                 285

Leu Glu Asp Leu Asn Arg Gln Leu Gln Gln Val Glu Glu Phe Arg
    290                 295                 300

Arg Thr Val Glu Pro Met Gly Glu Met Phe Asn Lys Ala Leu Val Gln
305                 310                 315                 320

Gln Leu Glu Gln Phe Arg Gln Gln Leu Gly Pro Asn Ser Gly Glu Val
                325                 330                 335

Glu Ser His Leu Ser Phe Leu Glu Lys Ser Leu Arg Glu Lys Val Asn
            340                 345                 350

Ser Phe Met Ser Thr Leu Glu Lys Lys Gly Ser Pro Asp Gln Pro Gln
        355                 360                 365

Ala Leu Pro Leu Pro Glu Gln Ala Gln Glu Gln Ala Gln Glu Gln Ala
    370                 375                 380

Gln Glu Gln Val Gln Pro Lys Pro Leu Glu Ser
385                 390                 395
```

-continued

<210> SEQ ID NO 31
<211> LENGTH: 401
<212> TYPE: PRT
<213> ORGANISM: Homo sapiens

<400> SEQUENCE: 31

Gly Ala Arg Ala Glu Val Ser Ala Asp Gln Val Ala Thr Val Met Trp
1               5                   10                  15

Asp Tyr Phe Ser Gln Leu Ser Ser Asn Ala Lys Glu Ala Val Glu His
            20                  25                  30

Leu Gln Lys Ser Glu Leu Thr Gln Gln Leu Asn Ala Leu Phe Gln Asp
        35                  40                  45

Lys Leu Gly Glu Val Asn Thr Tyr Ala Gly Asp Leu Gln Lys Lys Leu
    50                  55                  60

Val Pro Phe Ala Thr Glu Leu His Glu Arg Leu Ala Lys Asp Ser Lys
65                  70                  75                  80

Lys Leu Lys Glu Glu Ile Arg Lys Glu Leu Glu Glu Val Arg Ala Arg
                85                  90                  95

Leu Leu Pro His Ala Asn Glu Val Ser Gln Lys Ile Gly Glu Asn Val
            100                 105                 110

Arg Glu Leu Gln Gln Arg Leu Glu Pro Tyr Thr Asp Gln Leu Arg Thr
        115                 120                 125

Gln Val Asn Thr Gln Thr Glu Gln Leu Arg Arg Gln Leu Thr Pro Tyr
    130                 135                 140

Ala Gln Arg Met Glu Arg Val Leu Arg Glu Asn Ala Asp Ser Leu Gln
145                 150                 155                 160

Thr Ser Leu Arg Pro His Ala Asp Gln Leu Lys Ala Lys Ile Asp Gln
                165                 170                 175

Asn Val Glu Glu Leu Lys Gly Arg Leu Thr Pro Tyr Ala Asp Glu Phe
            180                 185                 190

Lys Val Lys Ile Asp Gln Thr Val Glu Glu Leu Arg Arg Ser Leu Ala
        195                 200                 205

Pro Tyr Ala Gln Asp Ala Gln Glu Lys Leu Asn His Gln Leu Glu Gly
    210                 215                 220

Leu Ala Phe Gln Met Lys Lys Asn Ala Glu Glu Leu Lys Ala Arg Ile
225                 230                 235                 240

Ser Ala Ser Ala Glu Glu Leu Arg Gln Arg Leu Ala Pro Leu Ala Glu
                245                 250                 255

Asp Met Arg Gly Asn Leu Arg Gly Asn Thr Glu Gly Leu Gln Lys Ser
            260                 265                 270

Leu Ala Glu Leu Gly Gly His Leu Asp Arg His Val Glu Glu Phe Arg
        275                 280                 285

Leu Arg Val Glu Pro Tyr Gly Glu Asn Phe Asn Lys Ala Leu Val Gln
    290                 295                 300

Gln Met Glu Gln Leu Arg Gln Lys Leu Gly Pro His Ala Gly Asp Val
305                 310                 315                 320

Glu Gly His Leu Ser Phe Leu Glu Lys Asp Leu Arg Asp Lys Val Asn
                325                 330                 335

Ser Phe Phe Ser Thr Phe Lys Glu Lys Glu Ser Gln Asp Asn Thr Leu
            340                 345                 350

Ser Leu Pro Glu Pro Glu Gln Gln Gln Glu Gln Gln Gln Glu Gln Glu
        355                 360                 365

Gln Gln Gln Glu Gln Glu Glu Gln Gln Gln Glu Gln Gln Gln
    370                 375                 380

Glu Gln Glu Gln Gln Glu Gln Val Gln Met Leu Ala Pro Leu Glu
385                 390                 395                 400

Ser

<210> SEQ ID NO 32
<211> LENGTH: 382
<212> TYPE: PRT
<213> ORGANISM: Homo sapiens

<400> SEQUENCE: 32

Met Phe Leu Lys Ala Val Val Leu Ser Leu Ala Leu Val Ala Val Thr
1               5                   10                  15

Gly Ala Arg Ala Glu Val Asn Ala Asp Gln Val Ala Thr Val Met Trp
                20                  25                  30

Asp Tyr Phe Ser Gln Leu Gly Ser Asn Ala Lys Lys Ala Val Glu His
            35                  40                  45

Leu Gln Lys Ser Glu Leu Thr Gln Gln Leu Asn Thr Leu Phe Gln Asp
50                  55                  60

Lys Leu Gly Glu Val Asn Thr Tyr Thr Glu Asp Leu Gln Lys Lys Leu
65                  70                  75                  80

Val Pro Phe Ala Thr Glu Leu His Glu Arg Leu Thr Lys Asp Ser Glu
                85                  90                  95

Lys Leu Lys Glu Glu Ile Arg Arg Glu Leu Glu Glu Leu Arg Ala Arg
            100                 105                 110

Leu Leu Pro His Ala Thr Glu Val Ser Gln Lys Ile Gly Asp Asn Val
        115                 120                 125

Arg Glu Leu Gln Gln Arg Leu Gly Pro Phe Thr Gly Gly Leu Arg Thr
130                 135                 140

Gln Val Asn Thr Gln Val Gln Gln Leu Gln Arg Gln Leu Lys Pro Tyr
145                 150                 155                 160

Ala Glu Arg Met Glu Ser Val Leu Arg Gln Asn Ile Arg Asn Leu Glu
                165                 170                 175

Ala Ser Val Ala Pro Tyr Ala Asp Glu Phe Lys Ala Lys Ile Asp Gln
            180                 185                 190

Asn Val Glu Glu Leu Lys Gly Ser Leu Thr Pro Tyr Ala Glu Glu Leu
        195                 200                 205

Lys Ala Lys Ile Asp Gln Asn Val Glu Glu Leu Arg Arg Ser Leu Ala
210                 215                 220

Pro Tyr Ala Gln Asp Val Gln Glu Lys Leu Asn His Gln Leu Glu Gly
225                 230                 235                 240

Leu Ala Phe Gln Met Lys Lys Gln Ala Glu Glu Leu Lys Ala Lys Ile
                245                 250                 255

Ser Ala Asn Ala Asp Glu Leu Arg Gln Lys Leu Val Pro Val Ala Glu
            260                 265                 270

Asn Val His Gly His Leu Lys Gly Asn Thr Glu Gly Leu Gln Lys Ser
        275                 280                 285

Leu Leu Glu Leu Arg Ser His Leu Asp Gln Gln Val Glu Glu Phe Arg
290                 295                 300

Leu Lys Val Glu Pro Tyr Gly Glu Thr Phe Asn Lys Ala Leu Val Gln
305                 310                 315                 320

Gln Val Glu Asp Leu Arg Gln Lys Leu Gly Pro Leu Ala Gly Asp Val
                325                 330                 335

Glu Gly His Leu Ser Phe Leu Glu Lys Asp Leu Arg Asp Lys Val Asn
            340                 345                 350

Thr Phe Phe Ser Thr Leu Lys Glu Glu Ala Ser Gln Gly Gln Ser Gln
            355                 360                 365

Ala Leu Pro Ala Gln Glu Lys Ala Gln Ala Pro Leu Glu Gly
    370                 375                 380

<210> SEQ ID NO 33
<211> LENGTH: 391
<212> TYPE: PRT
<213> ORGANISM: Homo sapiens

<400> SEQUENCE: 33

Met Phe Leu Lys Ala Val Val Leu Thr Val Ala Leu Val Ala Ile Thr
1               5                   10                  15

Gly Thr Gln Ala Glu Val Thr Ser Asp Gln Val Ala Asn Val Met Trp
            20                  25                  30

Asp Tyr Phe Thr Gln Leu Ser Asn Asn Ala Lys Glu Ala Val Glu Gln
        35                  40                  45

Leu Gln Lys Thr Asp Val Thr Gln Gln Leu Asn Thr Leu Phe Gln Asp
    50                  55                  60

Lys Leu Gly Asn Ile Asn Thr Tyr Ala Asp Asp Leu Gln Asn Lys Leu
65                  70                  75                  80

Val Pro Phe Ala Val Gln Leu Ser Gly His Leu Thr Lys Glu Thr Glu
                85                  90                  95

Arg Val Arg Glu Glu Ile Gln Lys Glu Leu Glu Asp Leu Arg Ala Asn
            100                 105                 110

Met Met Pro His Ala Asn Lys Val Ser Gln Met Phe Gly Asp Asn Val
        115                 120                 125

Gln Lys Leu Gln Glu His Leu Arg Pro Tyr Ala Thr Asp Leu Gln Ala
    130                 135                 140

Gln Ile Asn Ala Gln Thr Gln Asp Met Lys Arg Gln Leu Thr Pro Tyr
145                 150                 155                 160

Ile Gln Arg Met Gln Thr Thr Ile Gln Asp Asn Val Glu Asn Leu Gln
                165                 170                 175

Ser Ser Met Val Pro Phe Ala Asn Glu Leu Lys Glu Lys Phe Asn Gln
            180                 185                 190

Asn Met Glu Gly Leu Lys Gly Gln Leu Thr Pro Arg Ala Asn Glu Leu
        195                 200                 205

Lys Ala Thr Ile Asp Gln Asn Leu Glu Asp Leu Arg Ser Arg Leu Ala
    210                 215                 220

Pro Leu Ala Glu Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Thr Asn Ile Asp Gln Leu Gln Lys Asn Leu Ala Pro Leu Val Glu
            260                 265                 270

Asp Val Gln Ser Lys Leu Lys Gly Asn Thr Glu Gly Leu Gln Lys Ser
        275                 280                 285

Leu Glu Asp Leu Asn Lys Gln Leu Asp Gln Gln Val Glu Val Phe Arg
    290                 295                 300

Arg Ala Val Glu Pro Leu Gly Asp Lys Phe Asn Met Ala Leu Val Gln
305                 310                 315                 320

Gln Met Glu Lys Phe Arg Gln Gln Leu Gly Ser Asp Ser Gly Asp Val
                325                 330                 335

Glu Ser His Leu Ser Phe Leu Glu Lys Asn Leu Arg Glu Lys Val Ser
            340                 345                 350

```
Ser Phe Met Ser Thr Leu Gln Lys Lys Gly Ser Pro Asp Gln Pro Leu
            355                 360                 365

Ala Leu Pro Leu Pro Glu Gln Val Gln Glu Gln Val Gln Glu Gln Val
    370                 375                 380

Gln Pro Lys Pro Leu Glu Ser
385                 390

<210> SEQ ID NO 34
<211> LENGTH: 285
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I
<220> FEATURE:
<221> NAME/KEY: MOD_RES
<222> LOCATION: (1)..(1)
<223> OTHER INFORMATION: Ala, Gly, Ser or Thr

<400> SEQUENCE: 34

Xaa Pro Ile Val Asn Ala Lys Lys Asp Val Val Asn Thr Lys Met Phe
1               5                   10                  15

Glu Glu Leu Lys Ser Arg Leu Asp Thr Leu Ala Gln Glu Val Ala Leu
            20                  25                  30

Leu Lys Glu Gln Gln Ala Leu Gln Thr Val Asp Glu Pro Pro Gln Ser
        35                  40                  45

Pro Trp Asp Arg Val Lys Asp Leu Ala Thr Val Tyr Val Asp Val Leu
    50                  55                  60

Lys Asp Ser Gly Arg Asp Tyr Val Ser Gln Phe Glu Gly Ser Ala Leu
65                  70                  75                  80

Gly Lys Gln Leu Asn Leu Lys Leu Leu Asp Asn Trp Asp Ser Val Thr
                85                  90                  95

Ser Thr Phe Ser Lys Leu Arg Glu Gln Leu Gly Pro Val Thr Gln Glu
            100                 105                 110

Phe Trp Asp Asn Leu Glu Lys Glu Thr Glu Gly Leu Arg Gln Glu Met
        115                 120                 125

Ser Lys Asp Leu Glu Glu Val Lys Ala Lys Val Gln Pro Tyr Leu Asp
    130                 135                 140

Asp Phe Gln Lys Lys Trp Gln Glu Glu Met Glu Leu Tyr Arg Gln Lys
145                 150                 155                 160

Val Glu Pro Leu Arg Ala Glu Leu Gln Glu Gly Ala Arg Gln Lys Leu
                165                 170                 175

His Glu Leu Gln Glu Lys Leu Ser Pro Leu Gly Glu Glu Met Arg Asp
            180                 185                 190

Arg Ala Arg Ala His Val Asp Ala Leu Arg Thr His Leu Ala Pro Tyr
        195                 200                 205

Ser Asp Glu Leu Arg Gln Arg Leu Ala Ala Arg Leu Glu Ala Leu Lys
    210                 215                 220

Glu Asn Gly Gly Ala Arg Leu Ala Glu Tyr His Ala Lys Ala Thr Glu
225                 230                 235                 240

His Leu Ser Thr Leu Ser Glu Lys Ala Lys Pro Ala Leu Glu Asp Leu
                245                 250                 255

Arg Gln Gly Leu Leu Pro Val Leu Glu Ser Phe Lys Val Ser Phe Leu
            260                 265                 270

Ser Ala Leu Glu Glu Tyr Thr Lys Lys Leu Asn Thr Gln
        275                 280                 285
```

```
<210> SEQ ID NO 35
<211> LENGTH: 307
<212> TYPE: PRT
<213> ORGANISM: Artificial Sequence
<220> FEATURE:
<223> OTHER INFORMATION: Description of Artificial Sequence: Synthetic
      Tetranectin-apolipoprotein A-I with N-terminal His-tag
<220> FEATURE:
<221> NAME/KEY: MOD_RES
<222> LOCATION: (8)..(24)
<223> OTHER INFORMATION: This region may encompass AP, GP, SP, PP, GSAP,
      GSGP, GSSP, GSPP, GGGS, GGGGS, GGGSGGGS, GGGGSGGGGS, GGGSGGGSGGGS,
      GGGGSGGGGSGGGGS, GGGSAP, GGGSGP, GGGSSP, GGGSPP, GGGGSAP,
      GGGGSGP, GGGGSSP, GGGGSPP, GGGSGGGSAP, GGGSGGGSGP,
<220> FEATURE:
<221> NAME/KEY: MOD_RES
<222> LOCATION: (8)..(24)
<223> OTHER INFORMATION: Continued from above; GGGSGGGSSP, GGGSGGGSPP,
      GGGSGGGSGGGSAP, GGGSGGGSGGGSGP, GGGSGGGSGGGSSP, GGGSGGGSGGGSPP,
      GGGGSGGGGSAP, GGGGSGGGGSGP, GGGGSGGGGSSP, GGGGSGGGGSPP,
      GGGGSGGGGSGGGGSAP, GGGGSGGGGSGGGGSGP, GGGGSGGGGSGGGGSSP or
      GGGGSGGGGSGGGGSPP

<400> SEQUENCE: 35

Met His His His His His Xaa Xaa Xaa Xaa Xaa Xaa Xaa Xaa Xaa
1               5                   10                  15

Xaa Xaa Xaa Xaa Xaa Xaa Xaa Xaa Ile Val Asn Ala Lys Lys Asp Val
            20                  25                  30

Val Asn Thr Lys Met Phe Glu Glu Leu Lys Ser Arg Leu Asp Thr Leu
        35                  40                  45

Ala Gln Glu Val Ala Leu Leu Lys Glu Gln Gln Ala Leu Gln Thr Val
    50                  55                  60

Asp Glu Pro Pro Gln Ser Pro Trp Asp Arg Val Lys Asp Leu Ala Thr
65                  70                  75                  80

Val Tyr Val Asp Val Leu Lys Asp Ser Gly Arg Asp Tyr Val Ser Gln
                85                  90                  95

Phe Glu Gly Ser Ala Leu Gly Lys Gln Leu Asn Leu Lys Leu Leu Asp
            100                 105                 110

Asn Trp Asp Ser Val Thr Ser Thr Phe Ser Lys Leu Arg Glu Gln Leu
        115                 120                 125

Gly Pro Val Thr Gln Glu Phe Trp Asp Asn Leu Glu Lys Glu Thr Glu
    130                 135                 140

Gly Leu Arg Gln Glu Met Ser Lys Asp Leu Glu Glu Val Lys Ala Lys
145                 150                 155                 160

Val Gln Pro Tyr Leu Asp Asp Phe Gln Lys Lys Trp Gln Glu Glu Met
                165                 170                 175

Glu Leu Tyr Arg Gln Lys Val Glu Pro Leu Arg Ala Glu Leu Gln Glu
            180                 185                 190

Gly Ala Arg Gln Lys Leu His Glu Leu Gln Glu Lys Leu Ser Pro Leu
        195                 200                 205

Gly Glu Glu Met Arg Asp Arg Ala Arg Ala His Val Asp Ala Leu Arg
    210                 215                 220

Thr His Leu Ala Pro Tyr Ser Asp Glu Leu Arg Gln Arg Leu Ala Ala
225                 230                 235                 240

Arg Leu Glu Ala Leu Lys Glu Asn Gly Gly Ala Arg Leu Ala Glu Tyr
                245                 250                 255

His Ala Lys Ala Thr Glu His Leu Ser Thr Leu Ser Glu Lys Ala Lys
            260                 265                 270

Pro Ala Leu Glu Asp Leu Arg Gln Gly Leu Leu Pro Val Leu Glu Ser
        275                 280                 285
```

```
Phe Lys Val Ser Phe Leu Ser Ala Leu Glu Glu Tyr Thr Lys Lys Leu
    290                 295                 300

Asn Thr Gln
305

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      fragment of an interferon sequence

<400> SEQUENCE: 36

Cys Asp Leu Pro Gln Thr His Ser Leu
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      hexa-histidine tag

<400> SEQUENCE: 37

His His His His His His
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      IgA protease cleavage

<400> SEQUENCE: 38

Val Val Ala Pro Pro Ala Pro
1               5
```

ALKALINE FEED

CROSS-REFERENCE TO RELATED APPLICATIONS

This Application claims priority under 35 U.S.C. §119 to European Application No. EP 10008997.8 filed Aug. 30, 2010, the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 18, 2012, is named P4519.txt and is 86,747 bytes in size.

FIELD OF THE INVENTION

Herein is reported a method for high cell density cultivation of a prokaryotic cell, such as an *Escherichia coli* strain, in a chemically defined medium for the production of a polypeptide wherein an amino acid is fed by a concentrated alkaline solution simultaneously regulating the pH of the cultivation medium and acting as a nitrogen source.

BACKGROUND OF THE INVENTION

In recent years the production of proteins has steadily increased and it is likely that proteins will become the biggest group of therapeutics available for the treatment of various diseases in the near future. The impact of proteins emerges from their specificity, such as the specific target recognition and binding function.

Cell cultures are used in fermentative processes to produce substances and in particular proteins. A distinction is made between processes in which the cell cultures are genetically unmodified and form their own metabolic products and processes in which the organisms are genetically modified in such a manner that they either produce a larger amount of their own substances such as proteins or produce foreign substances. The organisms producing the substances are supplied with a nutrient medium which guarantees the survival of the organisms and enables the production of the desired target compound. Numerous culture media are known for these purposes which enable an optimal cultivation of the specific host.

High-cell-density cultivation of *Escherichia coli* is reported by Riesenberg (Riesenberg, D., et al., Curr. Opin. Biotechnol. 2 (1991) 380-384) and Horn (Horn, U., et al., Appl. Microbiol. Biotechnol. 46 (1996) 524-532). Riesenberg, D. and Guthke, R. (Appl. Microbiol. Biotechnol. 51 (1999) 422-430) reported the high-cell-density cultivation of microorganisms. Growing *E. coli* to high cell density is reviewed by Shiloach, J. and Fass, R. (Biotechnol. Advances 23 (2005) 345-357).

In WO 91/10721 a process for high cell density fermentation of *Escherichia coli* in an agitated boiler fermenter is reported. A method of plasmid DNA production and purification is reported in WO 97/29190. The controlling of growth of aerobic submerged microorganism cultures by controlling dissolved oxygen concentration and oxygen transfer rate is reported in DD 295867. In EP 0 866 876 a process for the preparation of recombinant proteins in *E. coli* by high cell density fermentation is reported.

In WO 03/048374 a process for the production of aromatic amino acid metabolite or derivative thereof is reported. A process for the preparation of recombinant proteins in *E. coli* by high cell density fermentation is reported in WO 97/21829.

SUMMARY OF THE INVENTION

It has been found that a prokaryotic cell, especially an amino acid auxotrophic *E. coli* K12 strain, can be cultivated on chemically defined medium at high cell densities if an amino acid is added to the cultivation medium in an alkaline solution.

One aspect as reported herein is a method for cultivating a bacterial cell, especially an *E. coli* cell, at high cell densities, wherein the cell expresses a recombinant polypeptide, wherein the cultivating comprises the adding of an alkaline solution of an amino acid selected from aspartate, aspartic acid, glutamine, glutamic acid, glycine, histidine, isoleucine, leucine, lysine, methionine, phenylalanine, tryptophan and tyrosine during the cultivating, wherein the amino acid has a concentration in the alkaline solution that is higher than its solubility in water at 20° C. and at neutral pH, and wherein the dry cell weight of the cultivated bacterial cell is at one point in the cultivating at least 20 g/l.

One aspect as reported herein is a method for producing a polypeptide comprising:
  a) providing a bacterial cell, especially an *E. coli* cell, comprising a nucleic acid encoding a polypeptide,
  b) cultivating the provided cell,
  c) adjusting the pH value during the cultivating with an alkaline solution comprising an amino acid selected from aspartate, aspartic acid, glutamine, glutamic acid, glycine, histidine, isoleucine, leucine, lysine, methionine, phenylalanine, tryptophan and tyrosine,
  d) recovering the polypeptide from the cell or the cultivation medium and thereby producing the polypeptide.

Another aspect as reported herein is the use of an alkaline solution comprising an amino acid for adjusting the pH value during the cultivation of a bacterial cell.

Also an aspect as reported herein is the use of an alkaline solution of an amino acid as feed in the cultivation of a bacterial cell, wherein the amino acid is selected from aspartate, aspartic acid, glutamine, glutamic acid, glycine, histidine, isoleucine, leucine, lysine, methionine, phenylalanine, tryptophan and tyrosine and the cultivation is up to a dry cell weight of 20 g/l or more.

The following are specific embodiments of all aspects as outlined before.

In one embodiment the amino acid is a poorly water soluble amino acid. In one embodiment the bacterial cell is an amino acid auxotrophic cell and the auxotrophy is for an amino acid selected from aspartate, aspartic acid, glutamine, glutamic acid, glycine, histidine, isoleucine, leucine, lysine, methionine, phenylalanine, tryptophan and tyrosine. In another embodiment the bacterial cell is an *Escherichia coli* cell or mutant thereof. In a further embodiment the amino acid has a solubility in water at 20° C. of 50 g/l or less. In a further embodiment the amino acid has a solubility in water at 20° C. of 40 g/l or less. In also an embodiment the amino acid is selected from aspartate, aspartic acid, glutamine, glutamic acid, glycine, histidine, isoleucine, leucine, lysine, methionine, phenylalanine, tryptophan and tyrosine. In another embodiment the amino acid is selected from aspartate, aspartic acid, glutamine, glutamic acid, histidine, leucine, tryptophan and tyrosine. In one embodiment the amino acid is leucine. In still another embodiment the amino acid has a concentration in the alkaline solution that is higher than its solubility in water at 20° C. In one embodiment the solubility is two times higher, in another embodiment three times higher than the solubility in water at 20° C. In another embodiment the solubility is higher than the solubility in water at 20° C. and at a pH value of pH 6 to 8. In one embodiment the amino acid has a concentration of 25 g/l or more in the alkaline solution, or in a further embodiment of 30 g/l or more, or in still another embodiment of 35 g/l or more. In one embodiment the amino acid has a concentration of 45 g/l or more in the alkaline solution. In one embodiment the amino acid has a concentration of about 50 g/l in the alkaline solution. In a further embodiment the alkaline solution has a pH value of 9 or more, in a further embodiment of 10 or more, and still in another embodiment of 10.5 or more. In one embodiment the alkaline solution is an ammonia solution of more than 5% (w/v) or of 10% (w/v) or more or of 15% (w/v) or more. In one embodiment the alkaline solution is an ammonia solution of about 12.5% (w/v) in water. In also an embodiment the polypeptide is human apolipoprotein A1 or a derivative thereof. In a further embodiment the apolipoprotein A1 has an amino acid sequence selected from of SEQ ID NO: 01 to SEQ ID NO: 35.

In another embodiment, the invention provides a method for cultivating an *Escherichia coli* cell expressing a polypeptide, characterized in that the cultivating comprises the adding of an alkaline solution of an amino acid selected from aspartate, aspartic acid, glutamine, glutamic acid, glycine, histidine, isoleucine, leucine, lysine, methionine, phenylalanine, tryptophan and tyrosine during the cultivating, wherein the amino acid has a concentration in the alkaline solution that is higher than its solubility in water at 20° C. and at neutral pH, and the amino acid has a concentration of 30 g/l or more, and wherein the alkaline solution is an ammonia solution of 10% (w/v) or more, and wherein the dry cell weight of the cultivated bacterial cell is at one point in the cultivating at least 20 g/l.

In another embodiment, the invention provides a method for producing a polypeptide comprising:
  a) cultivating an *Escherichia coli* cell comprising a nucleic acid encoding the polypeptide,
  c) adjusting the pH value during the cultivating with an alkaline solution comprising an amino acid selected from aspartate, aspartic acid, glutamine, glutamic acid, glycine, histidine, isoleucine, leucine, lysine, methionine, phenylalanine, tryptophan and tyrosine, and
  d) recovering the polypeptide from the cell or the cultivation medium and thereby producing the polypeptide,
  wherein the amino acid has a concentration in the alkaline solution of 30 g/l or more, and
  wherein the alkaline solution is an ammonia solution of 10% (w/v) or more.

In certain embodiments, the method is characterized in that the bacterial cell is an amino acid auxotrophic cell and the auxotrophy is for an amino acid selected from aspartate, aspartic acid, glutamine, glutamic acid, glycine, histidine, isoleucine, leucine, lysine, methionine, phenylalanine, tryptophan and tyrosine.

In certain embodiments, the method is characterized in that the alkaline solution has a pH value of 9 or more.

In certain embodiments, the method is characterized in that the polypeptide is human apolipoprotein A1 or a derivative thereof.

In certain embodiments, the method is characterized in that the apolipoprotein A1 has an amino acid sequence selected from SEQ ID NO: 01 to 35.

In certain embodiments, the method is characterized in that the apolipoprotein A1 has an amino acid sequence selected from SEQ ID NO: 01, 02, 34, and 35.

In certain embodiments, the method is characterized in that the amino acid has a concentration of about 50 g/l.

In certain embodiments, the method is characterized in that the alkaline solution is an ammonia solution of about 12.5% (w/v) of ammonia in water.

In certain embodiments, the method is characterized in that the amino acid is leucine.

In certain embodiments, the method is characterized in that the alkaline solution comprises leucine and proline.

In certain embodiments, the method is characterized in that the alkaline solution is an ammonia solution of about 12.5% (w/v and comprises the amino acids leucine and proline each at a concentration of about 50 g/l.

In certain embodiments, the invention provides for use of an alkaline solution of an amino acid as feed in the cultivation of a bacterial cell, wherein the amino acid is selected from aspartate, aspartic acid, glutamine, glutamic acid, glycine, histidine, isoleucine, leucine, lysine, methionine, phenylalanine, tryptophan and tyrosine and the cultivation is up to a dry cell weight of 20 g/l or more and the amino acid has a concentration of 30 g/l or more in the alkaline solution and the alkaline solution is an ammonia solution of 10% (w/v) or more.

In certain embodiments, the invention provides for use according to embodiment 13, characterized in that the bacterial cell is an amino acid auxotrophic cell and the auxotrophy is for an amino acid selected from aspartate, aspartic acid, glutamine, glutamic acid, glycine, histidine, isoleucine, leucine, lysine, methionine, phenylalanine, tryptophan and tyrosine.

In certain embodiments, the method is characterized in that the *Escherichia coli* cell is an amino acid auxotrophic *Escherichia coli* cell.

DETAILED DESCRIPTION OF THE INVENTION

Figure 1:
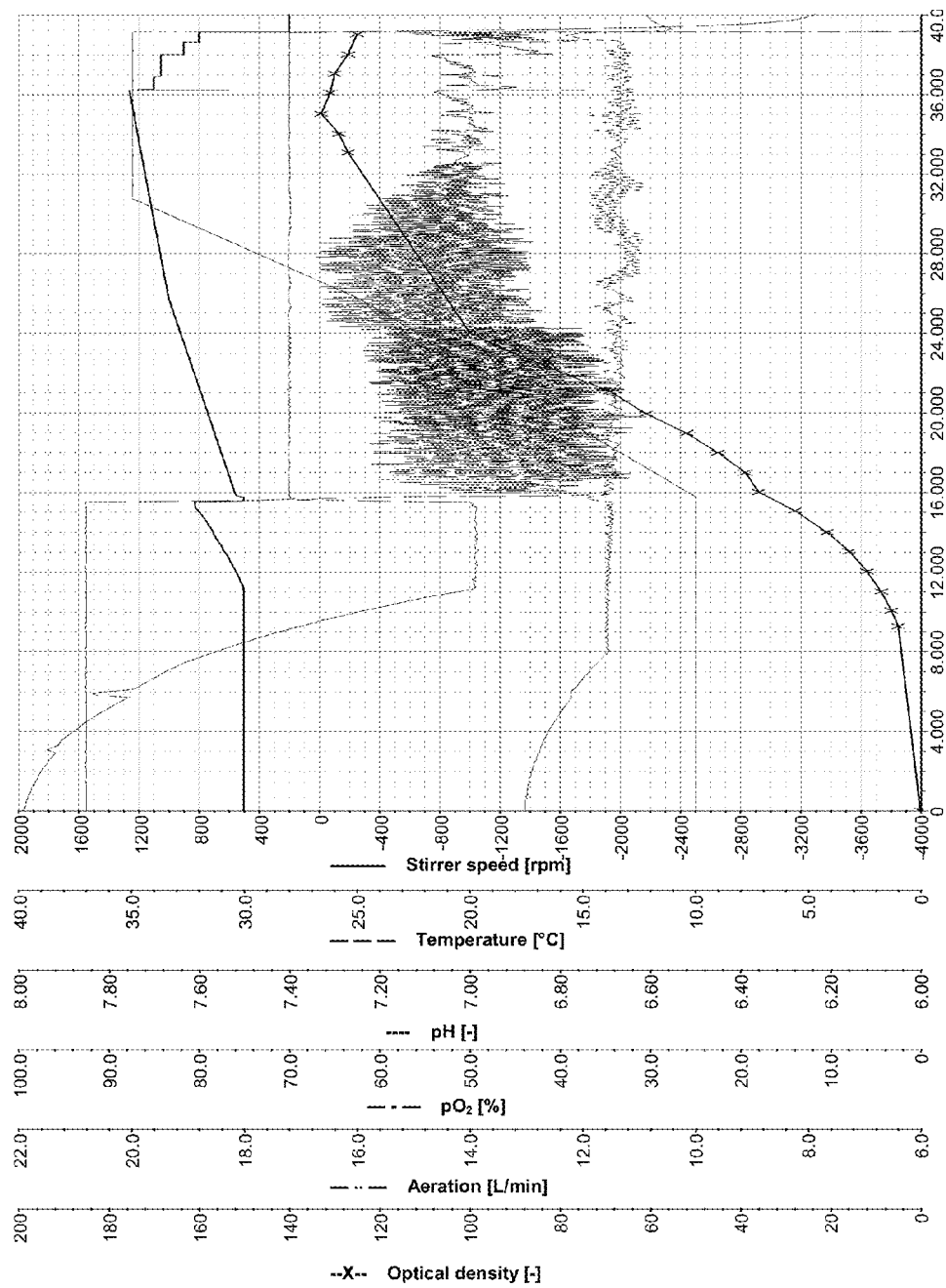
FIG. 1 Parameter plot Example 3—separate amino acid feeding.

Herein is reported a method for cultivating a prokaryotic cell, e.g. an amino acid auxotrophic bacterial cell, wherein at least one amino acid, e.g. that for which the cell is auxotrophic, is added in an alkaline solution.

It has been found that a prokaryotic cell, e.g. an amino acid auxotrophic *E. coli* K12 strain, can be cultivated at high cell densities if a feed comprising at least one amino acid, such as that for which the cell has an auxotrophy, is added to the cultivation medium in an alkaline solution. This is especially advantageous when the amino acid is poorly soluble in water and the solubility can be increased by dissolving the amino acid in an alkaline solution. At the same time the alkaline solution can be used to adjust the pH value of the cultivation medium. By combining the amino acid solution and the pH adjustment solution in a highly concentrated single feed solution the added volume can be reduced, thus, allowing for a high cell density cultivation of the prokaryotic cell. Additionally it has been found that a concentration of at least 45 g/l of the amino acid in the alkaline feed solution results in an increased production of a recombinant polypeptide.

In one embodiment the method for cultivating a prokaryotic cell comprises the following steps
 a) providing a prokaryotic cell,
 b) cultivating the prokaryotic cell,
 c) adjusting the pH value during the cultivating of the prokaryotic cell with an alkaline solution comprising an amino acid selected from aspartate, aspartic acid, glutamine, glutamic acid, glycine, histidine, isoleucine, leucine, lysine, methionine, phenylalanine, tryptophan and tyrosine.

An "amino acid auxotrophic prokaryotic cell" is a prokaryotic cell that cannot synthesize an essential amino acid e.g. due to a mutation or deletion within a gene locus comprising the structural gene encoding the proteins of the corresponding biosynthetic pathway. Without the addition of the respective amino acid to the cultivation medium the cell cannot proliferate. The auxotrophy can be for any amino acid. The prokaryotic cell can also be auxotrophic for more than one amino acid. Thus, in one embodiment the amino acid auxotrophic prokaryotic cell is auxotrophic for at least one amino acid. In another embodiment the amino acid auxotrophic prokaryotic cell is auxotrophic for at least one, at least two, at least three, at least four, at least five amino acids. In a further embodiment the amino acid auxotrophic prokaryotic cell is auxotrophic for up to 5, or up to 10, or up to 15 amino acids. In another embodiment the amino acid auxotrophic prokaryotic cell is auxotrophic for one to five amino acids, or one to three amino acids, or for one to two amino acids, or for one amino acid, or for two amino acids, or for three amino acids, or for four amino acids. The amino acid auxotrophic prokaryotic cell is in one embodiment a bacterial cell.

In one embodiment the bacterial cell is an *Escherichia* cell, or a *Bacillus* cell, or a *Lactobacillus* cell, or a *Corynebacterium* cell, or a Yeast cell (*Saccharomyces, Candida,* or *Pichia*). In a further embodiment the cell is an *Escherichia coli* cell, or a *Bacillus subtilis* cell, or a *Lactobacillus acidophilus* cell, or a *Corynebacterium glutamicum* cell, or a *Pichia pastoris* yeast cell.

The term "adjusting a value" denotes that the respective value is maintained at a predetermined level throughout a cultivating, i.e. the value is checked continuously or at predetermined constant time intervals and change by the addition of a correction fluid if the value is outside a preset acceptance range. For example, the term "adjusting the pH value" denotes that the pH value of a cultivation medium is determined periodically at fixed time points, i.e. with fixed time intervals, and if the determined pH value is outside an acceptance range, such as e.g. 0.1 pH units or 0.15 pH units or 0.2 pH units, the pH value is re-adjusted to the predetermined pH value by the addition of a correction fluid, such as an acid or an alkaline solution.

Methods for cultivating a prokaryotic cell and also for cultivating an amino acid auxotrophic prokaryotic cell are known to a person of skill in the art (see e.g. Riesenberg, D., et al., Curr. Opin. Biotechnol. 2 (1991) 380-384). The cultivating can be with any method. In one embodiment the cultivating is a batch cultivating, a fed-batch cultivating, a perfusion cultivating, a semi-continuous cultivating, or a cultivating with full or partial cell retention. The only requirement for the cultivating is that an alkaline solution has to be added. This addition can be a sole feed solution or as a combined feed and pH adjustment solution.

The cultivation medium used for the start of the cultivating of the cell can be any medium known to a person skilled in the art, whereby the concentration of the amino acid to be fed is in the medium less than 5 g/l, or less than 7.5 g/l, or less than 10 g/l. It has to be pointed out that the concentration of the respective compounds has to be chosen in a way that no negative interference with the growth of the cell is to be expected. In one embodiment is the medium a defined glucose-mineral salt medium.

In one embodiment the cultivating is a high cell density cultivating. The term "high cell density cultivating" denotes a cultivating method wherein the dry cell weight of the cultivated prokaryotic cell is at one point in the cultivating at least 10 g/l. In one embodiment the dry cell weight is at one point in the cultivating at least 20 g/l, or at least 50 g/l, or at least 100 g/l, or more than 100 g/l. In order to reach such a high cell density state the volume of feed and/or adjustment solutions added during the cultivating has to be as small as possible. Methods for the determination of dry cell weight are reported e.g. in Riesenberg, D., et al., Appl. Microbiol. Biotechnol. 34 (1990) 77-82.

The nutrients in the provided medium will be metabolized during the cultivation and have to be replenished in order to avoid a limitation. If an amino acid has a poor solubility only a lowly concentrated feed solution can be prepared and added. To provide the required amount of the amino acid a large volume of the feed solution has to be added. This results in an increase in the total cultivation volume, a dilution of the culture broth and, thus, is disadvantageous for a high cell density processes.

The solubility of the 20 naturally occurring amino acids is listed in the following Table.

TABLE

| amino acid | solubility in water [g/l] | at [° C.] | solubility [good/acceptable/ poorly] |
|---|---|---|---|
| alanine | 166.5 | 25 | good |
| arginine | 150 | 20 | good |
| aspartate | 22 | 20 | poorly |
| aspartic acid | 4 | 20 | poorly |
| cysteine | 280 | 20 | good |
| glutamine | 26 | 18 | poorly |
| glutamic acid | 11 | 25 | poorly |
| glycine | 225 | 20 | good |
| histidine | 38 | 20 | poorly |
| isoleucine | 40 | 20 | poorly |
| leucine | 24 | 20 | poorly |
| lysine | 300 | 20 | good |
| methionine | 48 | 20 | poorly |
| phenylalanine | 27 | 20 | poorly |
| proline | 1500 | 20 | good |
| serine | 364 | 20 | good |
| threonine | 90 | 20 | acceptable |
| tryptophane | 10 | 20 | poorly |
| tyrosine | 0.4 | 20 | poorly |
| valine | 88 | 20 | acceptable |

The solubility of the amino acids aspartate, aspartic acid, glutamine, glutamic acid, histidine, isoleucine, leucine, methionine, phenylalanine, tryptophan and tyrosine is below 50 g/l and, thus, these amino acids are termed to have a poor solubility in water.

For example, the amino acid leucine has a solubility in water at 20° C. of 24 g/l and, thus, is poorly soluble. In an alkaline solution comprising 12.5% (w/v) ammonia the solubility is increased to 76 g/l and, thus, is more than three times the solubility in water. At the same time the required feed volume is reduced by more than 60%. If at the same time the alkaline solution is also used to adjust the pH value of the cultivation the added volume can be reduced even more. For example, the amino acid tyrosine has a solubility in water at 20° C. of 0.4 g/l and, thus, is poorly soluble. In an alkaline solution comprising 12.5% (w/v) ammonia the solubility is increased to 39 g/l and, thus, is about one hundred times the solubility in water.

In one embodiment the amino acid is aspartate, aspartic acid, glutamine, glutamic acid, glycine, histidine, isoleucine, leucine, lysine, methionine, phenylalanine, tryptophan and/or tyrosine. In also an embodiment the amino acid is aspartate, aspartic acid, glutamine, glutamic acid, histidine, leucine, tryptophan and/or tyrosine. In one embodiment the amino acid is leucine. In one embodiment the amino acid is an amino acid that it poorly soluble in water of a pH value of about 7 at 20° C. In also an embodiment the amino acid is leucine and proline, or the amino acid is leucine and proline and tryptophan. In a further embodiment the amino acid has a solubility in the alkaline solution that is higher than the solubility in water at 20° C. In a further embodiment the solubility in the alkaline solution is of from two times to ten times the solubility in water at 20° C. In one embodiment the amino acid has a solubility in water of 40 g/l or less. In another embodiment the amino acid has a solubility in water of 30 g/l or less. In also an embodiment the amino acid has a solubility in the alkaline solution of 25 g/l or more. In a further embodiment the amino acid has a concentration in the alkaline solution of 30 g/l or more. In another embodiment the amino acid has a concentration in the alkaline solution of 35 g/l or more. In also an embodiment the amino acid has a solubility in the alkaline solution of 50 g/l or more.

In the following Table the cultivation results in a cultivation vessel with 10 l working volume of the same Leucine and Proline auxotrophic *E. coli* cell obtained with different feeding modes are shown.

TABLE

| experiment | feed | total biomass (dry matter) [g/l] | recombinant protein yield [g/l] | final cultivation volume [l] |
|---|---|---|---|---|
| 1 | separate feeds: 20 g/l L-Leucine 100 g/l L-Proline | 49.4 | 10.0 | 11.8 |
| 2 | separate feeds: 20 g/l L-Leucine 100 g/l L-Proline | 50.6 | 9.0 | 12.2 |
| 3 | combined feed: 12.5% (w/v) NH$_3$ solution containing 50 g/l L-Leucine and 50 g/l L-Proline | 75.7 | 16.5 | 10.2 |
| 4 | combined feed: 12.5% (w/v) NH$_3$ solution containing 33 g/l L-Leucine and 33 g/l L-Proline | 56.5 | 13.5 | 9.3 |

It can be seen that in Experiments 1 and 2, in which the two amino acids are added as separate feeds to the cultivation medium, the total biomass obtained at the end of the cultivation and the yield of recombinant protein is lower compared to Experiments 3 and 4, in which the amino acids are added as a combined alkaline feed that at the same time is used to adjust the pH value of the cultivation medium. Also the final cultivation volume in Experiments 3 and 4 does not exceed the working volume of the cultivation vessel as in Experiments 1 and 2.

In one embodiment the alkaline solution is a 12.5% (w/v) ammonia solution in water and comprises at least one amino acid at a concentration of about 50 g/l or more. In one embodiment the alkaline solution comprises Leucine and Proline at a concentration of about 50 g/l.

Prokaryotic cells that can be used in the method as reported herein can comprise one or more amino acid auxotrophies. For example, *E. coli* cells deficient in the Leucine biosynthetic pathway can be selected from the LeuB6 deficient cells 13-6, χ148, χ156, χ2224, χ462, χ463, χ474, χ478, χ515, χ65, χ697, χ760, 2000 k MSE248, 342-167, 342MG, 679-680, A586, A592, A593, AA100, AA7852, AA787, AB1102, AB1111, AB1115, AB1122, AB1129, AB113, AB1132, AB1133, AB114, AB1157, AB1157-D, AB1314, AB1330, AB1331, AB1881, AB1884, AB1885, AB188, CP78, CP79, CR34 Thy-, CR34 Thy-SR, CR34/308, CR34/313, CR34/399, CR34/43, CR34/454, CR34/500, CR34/7a, CS130, CS312, CS419, CS425, CS426, CS460, CS471, CS472, CS50, CS81, CS85, CSR06, CSR603, CSR603/pDR1996, CT28-3b, DA10, DA11, DB1161, DB1257, DE1878, DE1882, DE2345, DF225, DF41, JRG94, JS10 C600r-m-, T6R, P678SSR pro-, PA20SR, PA200 SR, PA201 SR, PA214SRT6R, PA265 SR, PA309, PDE70, PA340, PA340/T6, PA360, PA414, PAM161, PAM162, PAM163, PAM164, PAM660, PAT84, PB349, PB69, PC1, PC2, PC3, PC5, PC6, PC8, PJ1, PJ2, PJ3, PJ4, PJ5, PJ C600 (=CRSR), W208 SR AzR, W2660, LAM-, W945his, WA2127, WA2379, WA2548, WA2552, WA2574, WA2899, WA921, WA946, WA960, Y10, Y46, Y53, Y70, YYC100.

In one embodiment the prokaryotic cell is an *E. coli* K12 cell or an *E. coli* B cell.

In one embodiment the alkaline solution is a strongly alkaline solution. In another embodiment the alkaline solution has a pH value of pH 9 or more, or pH 10 or more, or pH 10.5 or more. In a further embodiment the solubility of the amino acid in the alkaline solution is at least twice the solubility of the amino acid in water.

In one embodiment the method for producing a polypeptide as reported herein comprising the following steps
a) providing an amino acid auxotrophic bacterial cell comprising a nucleic acid encoding the polypeptide,
b) cultivating the provided cell,
c) adjusting the pH value during the cultivating with an alkaline solution comprising an amino acid for which the bacterial cell is auxotrophic,
d) recovering the polypeptide from the cell or the cultivation medium and thereby producing the polypeptide.

The following examples are provided to aid the understanding of the present invention, the true scope of which is set forth in the appended claims. It is understood that modifications can be made in the procedures set forth without departing from the spirit of the invention.

Material and Methods

Optical density of the cultivations was measured with a DR2800 photometer (Hach-Lange, Dusseldorf, Germany) at 578 nm.

Protein concentration was determined densitometrically by comparing the volumes of a standard protein band with the band volumes of the produced protein within the fermentation samples on a SDS-Page gel.

Example 1

Determination of Solubility of Leucine in an Ammonia Solution

The calculated amount of Leucine was weighted into a 500 ml flask. After addition of 250 ml deionized water the solution is sterilized by autoclavation. Thereafter 250 ml of a 25% (w/v) ammonia solution is added and determined whether the Leucine was dissolved or not. After dissolution of the Leucine the final volume of the solution was determined. If it deviates notably from 500 ml the solution was prepared again with a reduced amount of water (see Table 3).

TABLE 3

| | Leucine concentration [g/l] | | | | | | | | |
|---|---|---|---|---|---|---|---|---|---|
| | 17 | 18 | 19 | 20 | 21 | 25 | 30 | 40 | 50 |
| water [ml] | 250 | 250 | 250 | 250 | 250 | 250 | 250 | 250 | 250 |
| ammonia solution [ml] | 250 | 250 | 250 | 250 | 250 | 250 | 250 | 250 | 250 |
| soluble | yes | yes | yes | yes | yes | yes | yes | yes | yes |
| final volume [ml] | 500 | 500 | 500 | 500 | 500 | 500 | 500 | 500 | 500 |

| | Leucine concentration [g/l] | | | | | | | | |
|---|---|---|---|---|---|---|---|---|---|
| | 60 | 70 | 71 | 72 | 73 | 74 | 75 | 76 | 77 |
| water [ml] | 250 | 250 | 250 | 250 | 250 | 250 | 250 | 250 | 250 |
| ammonia solution [ml] | 250 | 250 | 250 | 250 | 250 | 250 | 250 | 250 | 250 |
| soluble | yes | yes | yes | yes | yes | yes | yes | yes | no |
| final volume [ml] | 500 | 500 | 500 | 500 | 500 | 500 | 500 | 500 | 500 |

Example 2

Making and Description of the *E. coli* Expression Plasmids

The tetranectin-apolipoprotein A-I fusion polypeptide was prepared by recombinant means. The amino acid sequence of the expressed fusion polypeptide in N- to C-terminal direction is as follows:
  the amino acid methionine (M),
  a fragment of an interferon sequence that has the amino acid sequence of CDLPQTHSL (SEQ ID NO: 36),
  a GS linker,
  a hexa-histidine tag that has the amino acid sequence of HHHHHH (SEQ ID NO: 37),
  a GS linker,
  an IgA protease cleavage site that has the amino acid sequence of VVAPPAP (SEQ ID NO: 38), and
  a tetranectin-apolipoprotein A-I that has the amino acid sequence of SEQ ID NO: 02.

The tetranectin-apolipoprotein A-I fusion polypeptides as described above are precursor polypeptides from which the tetranectin-apolipoprotein A-I fusion polypeptides was released by enzymatic cleavage in vitro using IgA protease.

The precursor polypeptide encoding fusion gene was assembled with known recombinant methods and techniques by connection of appropriate nucleic acid segments. Nucleic acid sequences made by chemical synthesis were verified by DNA sequencing. The expression plasmid for the production of tetranectin-apolipoprotein A-I was prepared as follows.

Making of the *E. coli* Expression Plasmid

Plasmid 4980 (4980-pBRori-URA3-LACI-SAC) is an expression plasmid for the expression of core-streptavidin in *E. coli*. It was generated by ligation of the 3142 bp long EcoRI/CelII-vector fragment derived from plasmid 1966 (1966-pBRori-URA3-LACI-T-repeat; reported in EP-B 1 422 237) with a 435 bp long core-streptavidin encoding EcoRI/CelII-fragment.

The core-streptavidin *E. coli* expression plasmid comprises the following elements:
  the origin of replication from the vector pBR322 for replication in *E. coli* (corresponding to by position 2517-3160 according to Sutcliffe, J. G., et al., Quant. Biol. 43 (1979) 77-90),
  the URA3 gene of *Saccharomyces cerevisiae* coding for orotidine 5'-phosphate decarboxylase (Rose, M., et al., Gene 29 (1984) 113-124) which allows plasmid selection by complementation of *E. coli* pyrF mutant strains (uracil auxotrophy),
  the core-streptavidin expression cassette comprising
    the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al., (see before),
    the core-streptavidin gene,
    two bacteriophage-derived transcription terminators, the λ-T0 terminator (Schwarz, E., et al., Nature 272 (1978) 410-414) and the fd-terminator (Beck, E., and Zink, B., Gene 1-3 (1981) 35-58),
    the lacI repressor gene from *E. coli* (Farabaugh, P. J., Nature 274 (1978) 765-769).

The final expression plasmid for the expression of the tetranectin-apolipoprotein A-I precursor polypeptide was prepared by excising the core-streptavidin structural gene from vector 4980 using the singular flanking EcoRI and CelII restriction endonuclease cleavage site and inserting the EcoRII/CelII restriction site flanked nucleic acid encoding the precursor polypeptide into the 3142 bp long EcoRI/CelII-4980 vector fragment.

Example 3

Feeding of Leucine and Proline as Separate Solutions

In this reference example the cultivation of an auxotrophic *E. coli* strain with a high cell density cultivation method as reported by Riesenberg, et al., (1991, supra) in combination with separate feeding of the amino acids L-Leucine and L-Proline was performed.

The *E. coli* K12 strain CSPZ-2 (leuB, proC, trpE, th-1, ΔpyrF) was used. The strain was transformed with an expression plasmid for the production of a therapeutic protein and maintained as primary seed bank in ampoules containing 1 ml of the strain grown on defined pre-culture medium to an optical density (determined at 578 nm) of approximately 1 and 1 ml of glycerol 85% (v/v) and stored at −80° C.

The defined pre-culture medium was a M9 medium according to Sambrook, J., et al., Molecular Cloning: A Laboratory Manual, Second Edition, Cold Spring Harbor Laboratory Press, Cold Spring Harbor, N.Y. (1989) supplemented with
  1.0 g/l L-Leucine,
  1.0 g/l L-Proline, and
  1.0 mg/l Thiamine-HCl.

For fermentation a batch medium according to Riesenberg, et al., (1991, supra) was used:
27.6 g/l Glucose,
13.3 g/l $KH_2PO_4$,
4.0 g/l $(NH_4)_2HPO_4$,
1.7 g/l Citrate,
1.2 g/l $MgSO_4*7H_2O$,
60 mg/l Iron(III)citrate,
2.5 mg/l $CoCk_2*6H_2O$,
15 mg/l $MnCl_2*4H_2O$,
1.5 mg/l $CuCl_2*2H_2O$,
3 mg/l $H_3BO_3$,
2.5 mg/l $Na_2MoO_4*2H_2O$,
8 mg/l $Zn(CH_3COO)_2*2H_2O$,
8.4 mg/l Titriplex III, and
1.3 ml/l Synperonic 10% anti foam agent.

The batch medium was supplemented with
5.4 mg/l Thiamin-HCl, and
1.2 g/l 1-Leucine and 1-Proline respectively.

The feed 1 solution contained
700 g/l Glucose, and
19.7 g/l $MgSO_4*7H_2O$.

The feed 2 solution contained
20 g/l 1-Leucine.

The feed 3 solution contained
100 g/l 1-Proline.

Feed 2 and 3 were prepared by weighting the amino acid, dissolving the amino acids in water, and autoclaving the solution. Afterwards the pH value of the solution has been determined to be about 6.15 for feed 2 and about 6.43 for feed 3.

The alkaline solution employed for pH regulation was an aqueous 12.5% (w/v) $NH_3$ solution.

All components were dissolved in deionized water.

For pre-culture 300 ml M9-medium in a 1000 ml Erlenmeyer-flask with 3 baffles was inoculated with 2 ml of primary seed bank ampoule. The cultivation was performed on a rotary shaker for 13 hours at 37° C. until an optical density (determined at 578 nm) of 1-3 was reached.

The main fermentation was carried out in 10 l Biostat C DCU3 fermenter (Sartorius, Melsungen, Germany). Starting with 6.4 l sterile batch medium plus 300 ml pre-cultivation the batch fermentation was carried out at 37° C., pH 6.9±0.2, 500 mbar and an aeration rate of 10 l/min. After the initially supplemented glucose was depleted the temperature was shifted to 28° C. and the fermentation entered the fed-batch mode with dissolved oxygen (pO2) kept at 50% (DO-stat, see e.g. Shay, L. K., et al., (1987, infra)) and by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids was started when the pH reached the lower regulation limit, i.e. pH 6.70, with the addition of feed 2 (starting with 33.8 ml/h for 14 hours, and then increased to 97.6 ml/h) and feed 3 (starting with 6.8 ml/h for 14 hours, and then increased to 19.5 ml/h). The flow rates were calculated from a separate fermentation run (see example 4), to respectively apply exactly the same amount of amino acids to the cultivations independently from the feeding strategy. The expression of recombinant therapeutic protein was induced by the addition of 1 mM IPTG at an optical density of 70.

Figure 2:
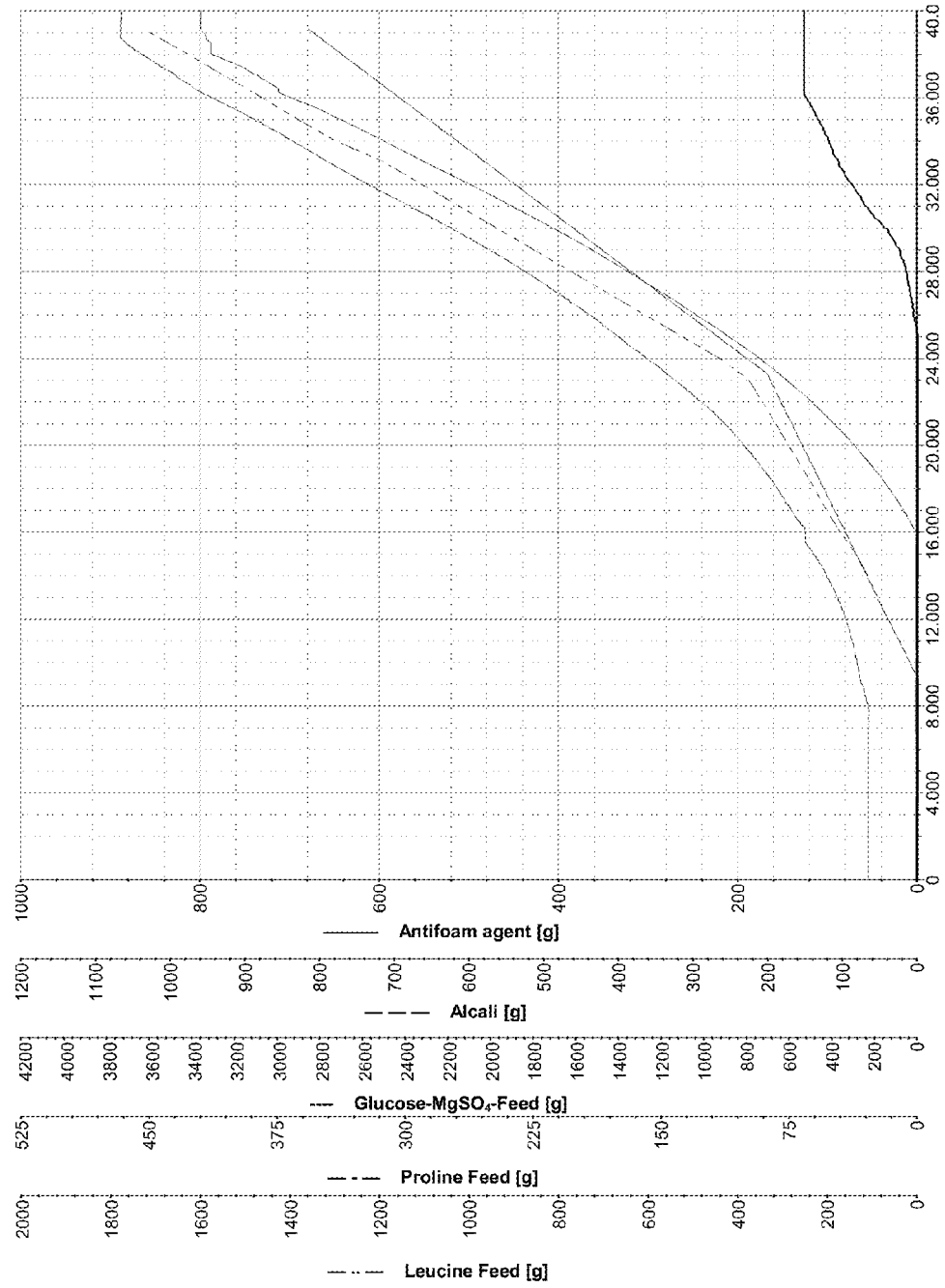
FIG. 2 Parameter plot Example 3—separate amino acid feeding.

The parameter plots of this fermentation are shown in FIGS. 1 and 2.

After inoculation followed by a short lag-phase, the cells were growing at maximum specific growth rate of $\mu max=0.30$ l/h. After 8 hours of cultivation the lower pH regulation limit was reached and the pH was controlled at 6.70 with the addition of a 12.5% $NH_4OH$ solution. Simultaneously the amino acid feeding was started by adding feed 2 and feed 3. After 16 hours the glucose was used up, indicated by the steep increase in pO2-value. At this time the cultivation temperature was shifted from 37° C. to 28° C. After additional 15 minutes the pO2-feed control was started and pO2 was controlled at 50% by the addition of feed 1 while continuously increasing agitation and aeration rate to their respective maxima of 1400 rpm and 20 l/min. The growth rate was continuously decreasing from 0.15 to approximately 0.05 l/h. Concomitantly the stirrer speed was reduced stepwise after 36 hours of cultivation. When no further increase in optical density could be determined the fermentation was terminated and bacteria cells where cooled to 4° C. over night before harvest.

At fermentation end the total biomass yield was 49.4 g/l (dry matter). During the fermentation almost no acetate was excreted but towards the end concentrations increased steeply to 7 g/l. The recombinant protein formation yielded 9.96 g/l. The volume of the culture broth exceeded the normal working volume of the fermenter vessel and increased to 11.8 l.

The fermentation was repeated and resulted in an end optical density of 130, end biomass yield of 50.6 g/l, and recombinant protein yield of 9.0 g/l, culture broth volume at the end of fermentation was 12.2 l.

Example 4

Feeding of Leucine and Proline Incorporated in Alkali Solution for pH Regulation In this fermentation amino acid feeding was incorporated in the alkaline pH control solution. The basis of this fermentation is the same high cell density cultivation method according to Riesenberg, et al., (1991, supra) as used in Example 3. The amino acids L-Leucine and L-Proline were incorporated in the aqueous 12.5% $NH_3$ solution and fed with alkali addition during pH control.

The *E. coli* K12 strain CSPZ-2 (leuB, proC, trpE, th-1, ΔpyrF) was used. The strain was transformed with an expression plasmid for the production of a therapeutic protein and maintained as primary seed bank in ampoules containing 1 ml of the strain grown on defined pre-culture medium to an optical density (determined at 578 nm) of approximately 1 and 1 ml of glycerol 85% (v/v) and stored at −80° C.

The defined pre-culture medium was a M9 medium according to Sambrook, J., et al., (Molecular Cloning: A Laboratory Manual, Second Edition, Cold Spring Harbor Laboratory Press, Cold Spring Harbor, N.Y. (1989)) supplemented with
1.0 g/l L-Leucine,
1.0 g/l L-proline, and
1.0 mg/l Thiamine-HCl.

For fermentation a batch medium according to Riesenberg, et al., (1991, supra) was used:
27.6 g/l Glucose,
13.3 g/l $KH_2PO_4$,
4.0 g/l $(NH_4)_2HPO_4$,
1.7 g/l Citrate,
1.2 g/l $MgSO_4*7H_2O$,
60 mg/l Iron(III)citrate,
2.5 mg/l $CoCl_2*6H_2O$,
15 mg/l $MnCl_2*4H_2O$,
1.5 mg/l $CuCl_2*2H_2O$,
3 mg/l $H_3BO_3$,
2.5 mg/l $Na_2MoO_4*2H_2O$, 8 mg/l $Zn(CH_3COO)_2*2H_2O$,
8.4 mg/l Titriplex III, and
1.3 ml/l Synperonic 10% anti foam agent.
The batch medium was supplemented with
5.4 mg/l Thiamin-HCl, and
1.2 g/l l-Leucine and l-Proline respectively.
The feed 1 solution contained
700 g/l Glucose, and
19.7 g/l $MgSO_4*7H_2O$.

The alkaline solution employed for pH regulation was an aqueous 12.5% (w/v) $NH_3$ solution supplemented with 50 g/l L-Leucine and 50 g/l L-Proline respectively.

All components were dissolved in deionized water.

The main fermentation was carried out in 10 l Biostat C DCU3 fermenter (Sartorius, Melsungen, Germany). Starting with 6.4 l sterile batch medium plus 300 ml pre-cultivation the batch fermentation was carried out at 37° C., pH 6.9±0.2, 500 mbar and an aeration rate of 10 l/min. After the initially supplemented glucose was depleted the temperature was shifted to 28° C. and the fermentation entered the fed-batch mode with dissolved oxygen (pO2) kept at 50% (DO-stat, see e.g. Shay, L. K., et al., (Shay, L. K., et al., J. Indus. Microbiol. 2 (1987) 79-85) and by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids resulted from the addition of alkali, when the pH reached the lower regulation limit of pH 6.70. From the time course of alkali addition the flow rates for feed 2 and 3 within example 2 were calculated, to respectively apply exactly the same amount of amino acids to the cultivations independently from the feeding strategy. The expression of recombinant therapeutic protein was induced by the addition of 1 mM IPTG at an optical density of 70.

Figure 3:
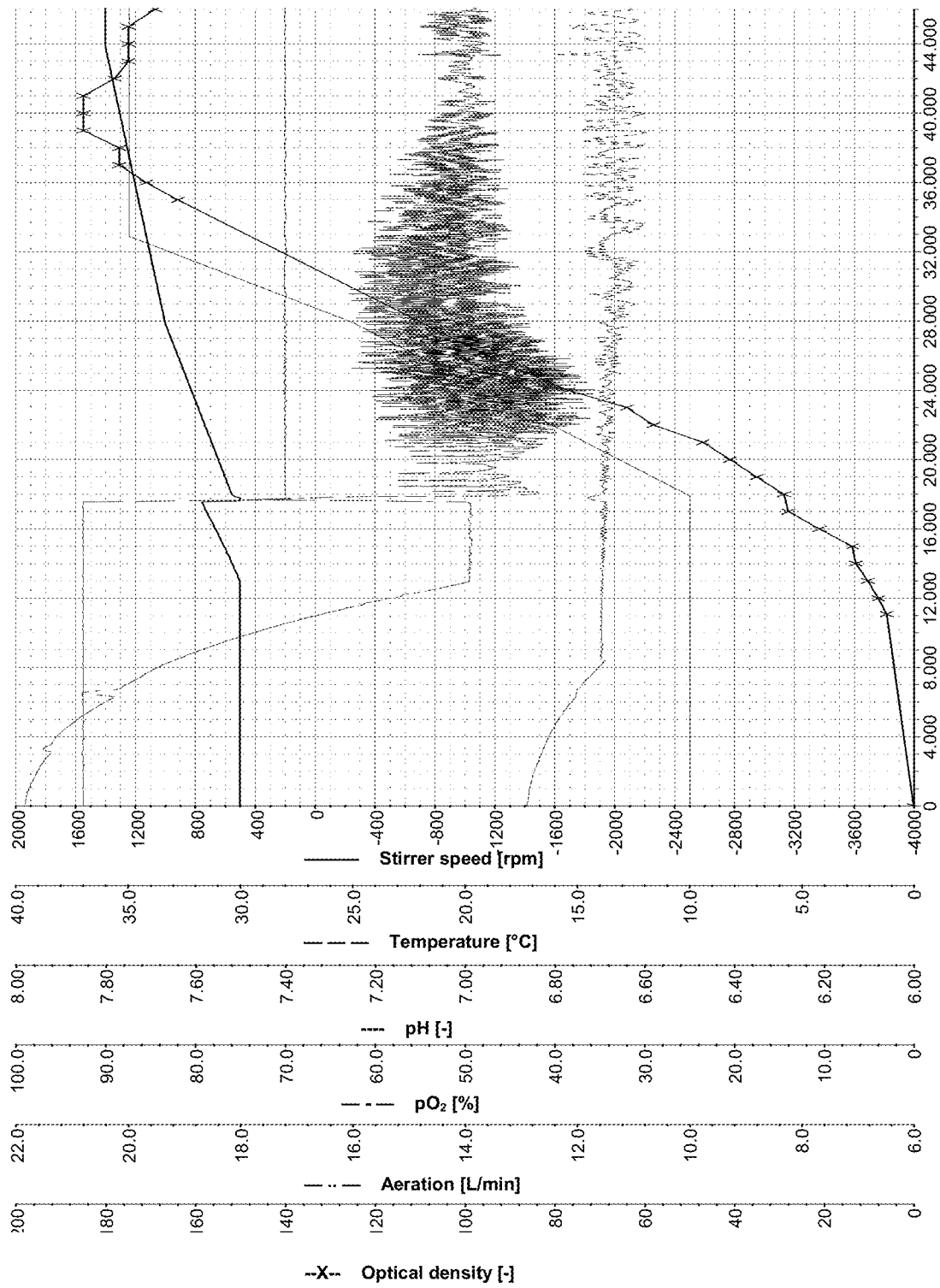
FIG. 3 Parameter plot Example 4—combined amino acid feeding.
Figure 4:
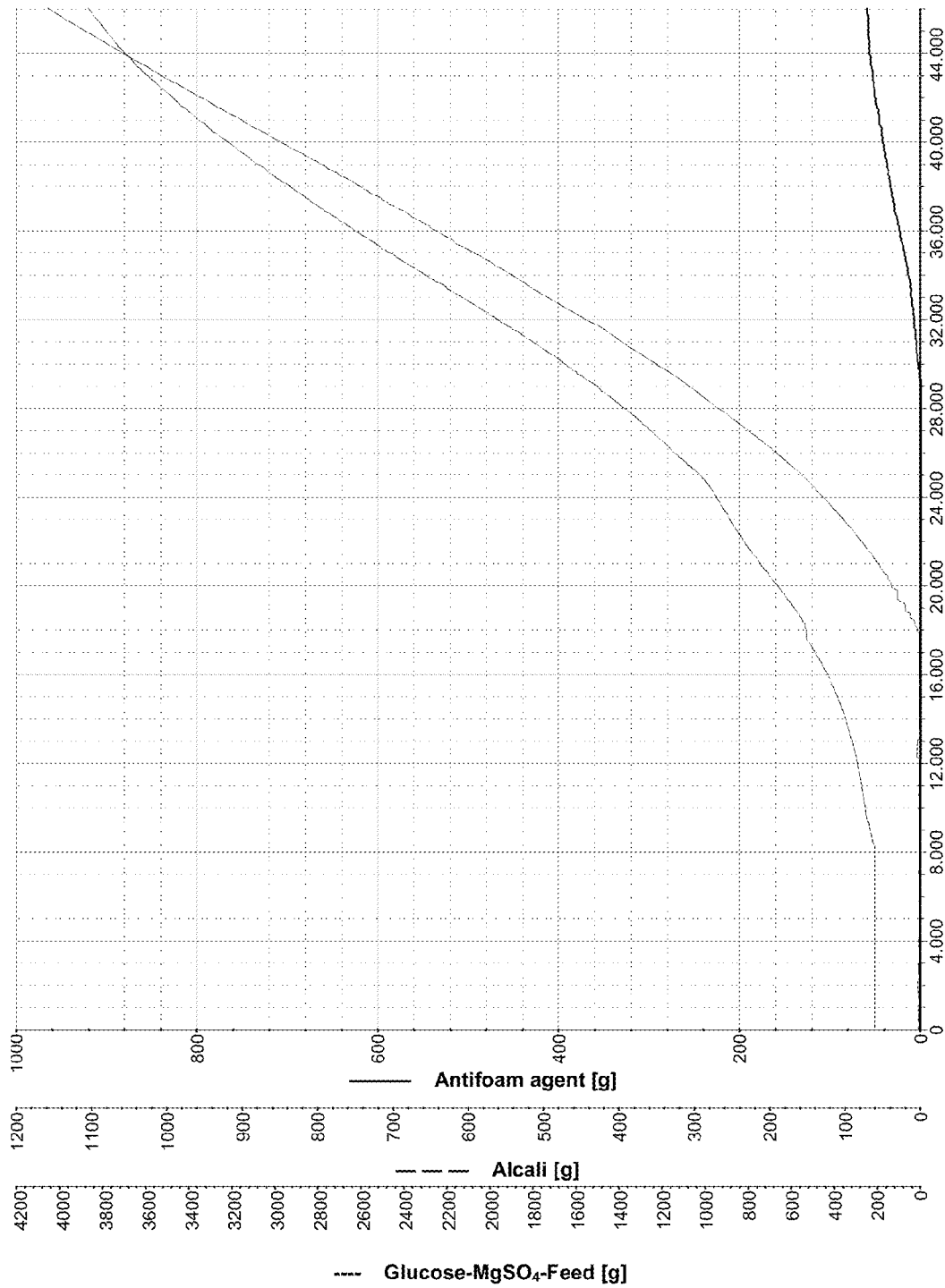
FIG. 4 Parameter plot Example 4—combined amino acid feeding.

The typically parameter plots of this fermentation are shown in FIGS. 3 and 4.

After inoculation followed by a short lag-phase the cells were growing at maximum specific growth rate of $\mu max=0.30$ l/h. After 8 hours of cultivation the lower pH regulation limit was reached and the pH was controlled at pH 6.70 with the addition of aqueous 12.5% $NH_3$ solution supplemented with 50 g/l L-Leucine and 50 g/l L-Proline respectively. This simultaneously starts the amino acid feeding. After 16 hours the provided glucose was used up. At this time the cultivation temperature was shifted from 37° C. to 28° C. After additional 15 minutes the pO2-feed control was started and pO2 was controlled at 50% by the addition of feed 1 while continuously increasing agitation and aeration rate to their respective maxima of 1400 rpm and 20 l/min. The growth rate was continuously decreasing from 0.15 to approximately 0.05 l/h. When no further increase in optical density was recognized, the fermentation was terminated and bacteria cells where cooled to 4° C. over night before harvest.

The optical density at fermentation end was 169 and the total biomass yield was 75.7 g/l (dry matter). During the fermentation almost no acetate was excreted and towards the end concentrations increased to 1 g/l. The recombinant protein formation yielded 16.5 g/l. The volume of the culture broth was 10.2 l.

The fermentation was repeated with different amounts of amino acids dissolved within the alkali solution (33 g/l of L-Leucine and L-Proline). The amount of fed amino acids was lower and resulted in an optical density of 145, end biomass yield of 56.5 g/l, and recombinant protein yield of 13.5 g/l, culture broth volume at the end of fermentation was 9.3 l.

The invention claimed is:

1. A method for cultivating an *Escherichia coli* cell expressing a polypeptide wherein the cultivating comprises adding an alkaline solution of an amino acid selected from aspartate, aspartic acid, glutamine, glutamic acid, glycine, histidine, isoleucine, leucine, lysine, methionine, phenylalanine, tryptophan and tyrosine during the cultivating;
   wherein the amino acid has a concentration in the alkaline solution that is higher than its solubility in water at 20° C. and at neutral pH, and the amino acid has a concentration of 30 g/l or more;
   wherein the alkaline solution is an ammonia solution of 10% (w/v) or more; and
   wherein the dry cell weight of the cultivated bacterial cell is at one point in the cultivating at least 20 g/l;
   wherein the polypeptide is an apolipoprotein A1 polypeptide having an amino acid sequence selected from SEQ ID NO: 01 through 35.

2. A method for producing a polypeptide, the method comprising:
   a) cultivating an *Escherichia coli* cell comprising a nucleic acid encoding the polypeptide;
   b) adjusting the pH value during the cultivating with an alkaline solution comprising an amino acid selected from aspartate, aspartic acid, glutamine, glutamic acid, glycine, histidine, isoleucine, leucine, lysine, methionine, phenylalanine, tryptophan and tyrosine; and
   c) recovering the polypeptide from the cell or the cultivation medium and thereby producing the polypeptide;
   wherein the amino acid has a concentration in the alkaline solution of 30 g/l or more, and
   wherein the alkaline solution is an ammonia solution of 10% (w/v) or more;
      wherein the polypeptide is an apolipoprotein A1 polypeptide having an amino acid sequence selected from SEQ ID NO: 01 through 35.

3. The method according to claim 1, wherein the bacterial cell is an amino acid auxotrophic cell and the auxotrophy is for an amino acid selected from aspartate, aspartic acid, glutamine, glutamic acid, glycine, histidine, isoleucine, leucine, lysine, methionine, phenylalanine, tryptophan and tyrosine.

4. The method according to claim 1, wherein the alkaline solution has a pH value of 9 or more.

5. The method according to claim 1, wherein the apolipoprotein A1 has an amino acid sequence selected from SEQ ID NO: 01, 02, 34, and 35.

6. The method according to claim 1, wherein the amino acid has a concentration of about 50 g/l.

7. The method according to claim 1, wherein the alkaline solution is an ammonia solution of about 12.5% (w/v) of ammonia in water.

8. The method according to claim 1, wherein the amino acid is leucine.

9. The method according to any claim 1, wherein the alkaline solution comprises leucine and proline.

10. The method according to claim 1, wherein the alkaline solution is an ammonia solution of about 12.5% (w/v and comprises the amino acids leucine and proline each at a concentration of about 50 g/l.

11. The method according to claim 1 wherein the *Escherichia coli* cell is an amino acid auxotrophic *Escherichia coli* cell.

* * * * *